(12) United States Patent
Biessen et al.

(10) Patent No.: US 9,134,320 B2
(45) Date of Patent: Sep. 15, 2015

(54) FUTURE CARDIAC EVENT BIOMARKERS CCL3, CCL5 AND CCL18

(75) Inventors: Ericus Anna Leonardus Biessen, Leiden (NL); Theodorus Josephus Cornelis Van Berkel, Haarlem (NL); Adriaan Otto Kraaijeveld, Leiden (NL)

(73) Assignees: Universiteit Leiden, Leiden (NL); Academisch Ziekenhuis Leiden, Leiden (NL)

( * ) Notice: Subject to any disclaimer, the term of this patent is extended or adjusted under 35 U.S.C. 154(b) by 793 days.

(21) Appl. No.: 12/677,437

(22) PCT Filed: Sep. 10, 2008

(86) PCT No.: PCT/IB2008/002771
§ 371 (c)(1),
(2), (4) Date: Jul. 6, 2010

(87) PCT Pub. No.: WO2009/034470
PCT Pub. Date: Mar. 19, 2009

(65) Prior Publication Data
US 2011/0059103 A1    Mar. 10, 2011

(30) Foreign Application Priority Data
Sep. 10, 2007 (GB) .................................. 0717637.3

(51) Int. Cl.
| | |
|---|---|
| G01N 33/53 | (2006.01) |
| C07K 16/24 | (2006.01) |
| C07K 14/52 | (2006.01) |
| G01N 33/68 | (2006.01) |

(52) U.S. Cl.
CPC ............ *G01N 33/6863* (2013.01); *G01N 33/53* (2013.01); *C07K 14/523* (2013.01); *C07K 16/24* (2013.01); *G01N 2333/523* (2013.01); *G01N 2500/10* (2013.01); *G01N 2800/226* (2013.01); *G01N 2800/323* (2013.01); *G01N 2800/324* (2013.01); *G01N 2800/325* (2013.01); *G01N 2800/50* (2013.01); *G01N 2800/52* (2013.01)

(58) Field of Classification Search
None
See application file for complete search history.

(56) References Cited

FOREIGN PATENT DOCUMENTS

WO    WO 01/66124    9/2001

OTHER PUBLICATIONS

Parissis et al, 2002 (J Inter Cyt Res. 22: 223-229).*
Jager et al (2005. Journal of Immunological Methods. 300: 124-135).*
Ardigo, D., et al., "Circulating Chemokines Accurately Identify Individuals with Clinically Significant Atherosclerotic Heart Disease", Physiological Genomics, vol. 31, No. 3, pp. 402-409, (2007).
Aukrust, P., et al., "Elevated Circulating Levels of C—C Chemokines in Patients with Congestive Heart Failure", Circulation, vol. 97, No. 12, pp. 1136-1143, (1998).
De Jager, S.C., et al., "CCL3 (MIP-1α) Levels are Elevated During Acute Coronary Syndromes and Show Strong Prognostic Power for Future Ischemic Events", Journal of Molecular and Cellular Cardiology, vol. 45, No. 3, pp. 446-452, (2008).
De Jager, S.C., et al., "Plasma Chemokine Profiling of Myocardial Infarction Patients by a Fluorescence Microsphere based Multiplex Assay Reveals Multiple Sensitive Chemokine Markers", Circulation, vol. 112, No. 17, pp. U161-U162, 78th Annual Scientific Session of the American-Heart-Association, (2005).
Parissis, J., et al., "Plasma Profiles of Peripheral Monocyte-related Inflammatory Markers in Patients with Arterial Hypertension. Correlations with Plasma Endothelin-1", International Journal of Cardiology, vol. 83, No. 1, pp. 13-21, (2002).
Vandervelde, S., et al., "Stem Cell-related Cardiac Gene Expression Early after Murine Myocardial Infarction", Cardiovascular Research, vol. 73, No. 4, pp. 783-793, (2007).

* cited by examiner

*Primary Examiner* — Zachary Howard
(74) *Attorney, Agent, or Firm* — Rebecca C. Riley-Vargas; Polsinelli PC

(57) ABSTRACT

The present invention relates to the identification of chemokine biomarkers predictive of future acute coronary syndromes including unstable angina pectoris (UAP). The present invention also identifies particular chemokines as potential therapeutic targets for intervention in cardiovascular diseases.

16 Claims, 19 Drawing Sheets

SEQUENCE LISTING

```
<160> NUMBER OF SEQ ID NOS: 22

<210> SEQ ID NO 1
<211> LENGTH: 23
<212> TYPE: DNA
<213> ORGANISM: Artificial
<220> FEATURE:
<223> OTHER INFORMATION: Primer

<400> SEQUENCE: 1
gaaatgtcag ttgctgcatt cct                                              23

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
acaatccgcc caaagggaac                                                  20

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
agtcttggca gtgcagatga a                                                21

<210> SEQ ID NO 4
<211> LENGTH: 28
<212> TYPE: DNA
```

```
<213> ORGANISM: Artificial
<220> FEATURE:
<223> OTHER INFORMATION: Primer

<400> SEQUENCE: 4
gaagatgaga acttcatcct aaagcata                                          28

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
tcctgctgac gattgacagg ta                                                22

<210> SEQ ID NO 6
<211> LENGTH: 17
<212> TYPE: DNA
<213> ORGANISM: Artificial
<220> FEATURE:
<223> OTHER INFORMATION: Primer

<400> SEQUENCE: 6
gtgcccgcaa ggcaaac                                                      17

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
ttcggcctga gtaactgtga aa                                                22

<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8
tgagtcatcc caagagtctc tgtc                                              24

<210> SEQ ID NO 9
<211> LENGTH: 18
<212> TYPE: DNA
<213> ORGANISM: Artificial
<220> FEATURE:
<223> OTHER INFORMATION: Primer

<400> SEQUENCE: 9
ctgctgcatg aacccggt                                                     18

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ggaagaagtg gcgaggtact                                                   20
```

```
<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11
actgtgggct cctccaaatt t                                             21

<210> SEQ ID NO 12
<211> LENGTH: 18
<212> TYPE: DNA
<213> ORGANISM: Artificial
<220> FEATURE:
<223> OTHER INFORMATION: Primer

<400> SEQUENCE: 12
tccatggtgg actgcgtg                                                 18

<210> SEQ ID NO 13
<211> LENGTH: 23
<212> TYPE: DNA
<213> ORGANISM: Artificial
<220> FEATURE:
<223> OTHER INFORMATION: Primer

<400> SEQUENCE: 13
agacatccgt tcccctacaa gaa                                           23

<210> SEQ ID NO 14
<211> LENGTH: 25
<212> TYPE: DNA
<213> ORGANISM: Artificial
<220> FEATURE:
<223> OTHER INFORMATION: Primer

<400> SEQUENCE: 14
cagggctccg atgtataata attga                                         25

<210> SEQ ID NO 15
<211> LENGTH: 23
<212> TYPE: DNA
<213> ORGANISM: Artificial
<220> FEATURE:
<223> OTHER INFORMATION: Primer

<400> SEQUENCE: 15
gtccacgttg atttctcctc atc                                           23

<210> SEQ ID NO 16
<211> LENGTH: 24
<212> TYPE: DNA
<213> ORGANISM: Artificial
<220> FEATURE:
<223> OTHER INFORMATION: Primer

<400> SEQUENCE: 16
cgtgtggtaa gtaaaattgc tgct                                          24

<210> SEQ ID NO 17
<211> LENGTH: 21
<212> TYPE: DNA
<213> ORGANISM: Artificial
<220> FEATURE:
```

```
<223> OTHER INFORMATION: Primer

<400> SEQUENCE: 17
cccagaagtg gttgtttccc t                                          21

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
tttccttgag cctggatgct                                            20

<210> SEQ ID NO 19
<211> LENGTH: 18
<212> TYPE: DNA
<213> ORGANISM: Artificial
<220> FEATURE:
<223> OTHER INFORMATION: Primer

<400> SEQUENCE: 19
tctgcgctcc tgcatctg                                              18

<210> SEQ ID NO 20
<211> LENGTH: 16
<212> TYPE: DNA
<213> ORGANISM: Artificial
<220> FEATURE:
<223> OTHER INFORMATION: Primer

<400> SEQUENCE: 20
cagtgggcgg gcaatg                                                16

<210> SEQ ID NO 21
<211> LENGTH: 21
<212> TYPE: DNA
<213> ORGANISM: Artificial
<220> FEATURE:
<223> OTHER INFORMATION: Primer

<400> SEQUENCE: 21
cctggaggcc acctcttcta a                                          21

<210> SEQ ID NO 22
<211> LENGTH: 25
<212> TYPE: DNA
<213> ORGANISM: Artificial
<220> FEATURE:
<223> OTHER INFORMATION: Primer

<400> SEQUENCE: 22
tgcagctcaa caatagaaat caatt                                      25
```

FUTURE CARDIAC EVENT BIOMARKERS CCL3, CCL5 AND CCL18

CROSS REFERENCE TO RELATED APPLICATIONS

This application is a U.S. National Stage Application under 35 U.S.C. 371 of PCT/IB2008/002771 filed on Sep. 10, 2008, which claims the benefit of GB 0717637.3, filed on Sep. 10, 2007, the contents of each of which are incorporated herein by reference in their entirety.

FIELD OF THE INVENTION

The present invention relates to the identification of chemokine biomarkers predictive of future acute coronary syndromes including unstable angina pectoris (UAP). The present invention also identifies particular chemokines as potential therapeutic targets for intervention in cardiovascular diseases.

BACKGROUND OF THE INVENTION

Acute coronary syndromes, including unstable angina pectoris (UAP), are associated with a high morbidity and mortality. In general, UAP results from erosion or rupture of a vulnerable atherosclerotic plaque superimposed by occlusive thrombus formation and distal ischemia[1]. Atherosclerosis is increasingly regarded as a dyslipidemic disorder with a strong inflammatory character[2]. These inflammatory processes are in part orchestrated by chemokines, which participate in the inflammatory process by mediating monocyte recruitment to sites of injury, vascular smooth muscle cell proliferation, neo-vascularisation and platelet activation[3-5]. Furthermore, chemokines appear to play a role in cardiac ischemia as well. Indeed ischemia was reported to lead to induced expression of chemokines in the myocardium or in the circulation, translating in the recruitment of leukocyte subsets and progenitor cells to the injury zone to contribute to the injury repair[6]. Given their diverse and deep impact in cardiovascular diseases, chemokines might not only serve as biomarkers of atherosclerosis, plaque disruption or ischemia, but also represent attractive therapeutic targets[7].

Approximately 50 chemokines have thus far been characterized and various are seen to be implicated in atherosclerosis and atherothrombosis[5]. In fact plasma levels of Regulated on Activation Normally T-cell Expressed and Secreted (RANTES or CCL5), Fractalkine (CX3CL1) and Monocyte Chemotactic Protein 1 (MCP-1 or CCL2) have already been shown in various studies to be altered in UAP or myocardial infarction[8-11]. Nevertheless, prospective data on chemokine plasma levels and/or chemokine receptor expression by circulating leukocyte subsets in acute coronary syndromes are lacking. Moreover, the use of such chemokines as markers of future coronary events has hitherto not been explored.

SUMMARY OF THE INVENTION

The present invention is based on a study to assess the levels of 11 chemokines in refractory unstable angina pectoris. The inventors examined baseline chemokine plasma patterns of a prospective cohort of patients with unstable angina pectoris by a high throughput multiplex assay, which allows simultaneous quantification of multiple chemokines in one single plasma sample[12]. For prospective analysis, differentially expressed chemokines at baseline were analysed in follow-up samples by ELISA. Furthermore, peripheral blood mononuclear cells (PBMCs) were examined for chemokine receptor expression.

In a first aspect the present invention provides the use of chemokine CCL3 and/or CCL18 and optionally CCL5 as a biomarker for the identification of whether or not a test subject is at increased risk of an acute cardiovascular syndrome or event.

CCL3 is also known as MIP-1α (macrophage inflammatory protein alpha) and LD78a/b; CCL18 is also known as PARC, DC-CK-1, AMAC-1 or MIP-4; and CCL-5 is also known as RANTES regulated on activation, normal T expressed and excreted and SISd.

The cardiovascular syndrome or event may comprise coronary artery disease, atherosclerosis, acute myocardial infarction, arteriosclerosis, unstable angina pectoris (UAP), embolism, deep vein thrombosis, stroke, congestive heart failure or arrhythmia.

Biomarker as used in the present invention means that the level of CCL3 and/or CCL18 and optionally CCL5 as determined (e.g. detected and/or quantified) in tissue sample or a sample of a body fluid of an individual is a predictive indicator for a future acute cardiovascular disorder as such and/or for monitoring the status and/or progression of a disorder. The detection of such biomarkers may also be used to monitor therapeutic regimes and/or clinical trials in order to detect whether or not a particular treatment may be effective.

The aforementioned cytokines may be identified in a sample of body fluid from a subject, or in cells obtained from a subject, such as from an atherosclerotic plaque, for example. The sample of a body fluid of an individual may be derived from blood, e.g. isolated mononuclear cells, or from a blood fraction, e.g. plasma or serum, especially plasma. For the purposes of the above aspects and embodiments, the subject may be a human or any other animal. In particular embodiments the subject is selected from the group consisting of human, non-human primate, equine, bovine, ovine, caprine, leporine, avian, feline or canine.

CC13, CC118 and/or CCL5 as used herein includes full-length protein, a protein fragment, a mutated protein, derivatives and secreting (producing) cells, e.g. leukocytes and receptors therefor. Fragments, mutants and derivatives of said chemokines are such that the biomarker characteristic of the chemokines is retained.

The use of the aforementioned chemokines as biomarkers according to the present invention means one or more of said chemokines is determined in said sample of an individual e.g. with detection means including those as conventional in the field of assays, e.g. immunoassays, chemokines is detected by an immunoassay such as enzyme linked immunoassays (ELISAs); fluorescence based assays, such as dissociation enhanced lanthanide fluoroimmunoassay (DELFIA), radiometric assays, multiplex immunoassays or cytometric bead assays (CBA); sensors. Detection means of the present invention include e.g. a molecule which specifically recognizes the particular chemokine, e.g. a molecule which is directly or indirectly detectable. Detection means of the present invention preferably comprise an antibody, including antibody derivatives or fragments thereof, e.g. an antibody which recognizes said chemokine(s) e.g. a label bearing chemokine recognising antibody.

The label may be one as conventional, e.g. biotin or an enzyme such as alkaline phosphatase (AP), horse radish peroxidase (HRP) or peroxidase (POD) or a fluorescent molecule, e.g. a fluorescent dye, such as e.g. fluorescein isothiocyanate. The label bearing molecule, e.g. the label bearing antibody, may be detected according to methods as conventional, e.g. via fluorescence measurement or enzyme detection methods.

CCL3, CCL18 and/or CCL5 secreting cells in a sample of a body fluid of an individual, e.g. blood, may be determined using conventional methods such as e.g. as described below. Cells may be purified, e.g. separated by a density gradient, from the sample, e.g. blood, and the purified cells obtained are stained. Anti-CCL18/3/5 antibodies, e.g. fluorescence labeled anti-CCL18/3/5 antibodies, may be added to the stained cell preparation, optionally after stimulation of the cells, e.g. with interleukin-4, and the level of CCL18/3/5 secretion by cells or CCL18/3/5-secreting cells determined or expression of the CCL18 and/or 3 and optionally CCL5 receptor(s) determined.

Optionally, the CCL18 and/or CCL3 and optionally CCL5 comprised in the sample or the CCL18/3/5 recognising e.g. detectable, molecule comprised in the detection means, may be immobilised on a solid phase. An appropriate solid phase includes e.g. one as conventional, e.g. a plastic plate like a polystyrene or polyvinyl plate, especially a microtiter plate. Also microbeads can be used as a solid phase, e.g. coated microbeads. The solid phase can be coated with a coating material the nature of which depends e.g. on the label comprised in the detection means. The coating material should be able to bind to the label, e.g. the label may be biotin and the coating material includes streptavidin, e.g. covalently bound to the solid phase.

In another aspect the present invention provides a method for screening and/or in vitro diagnosing whether or not an individual is at increased risk of an acute cardiovascular syndrome or disorder, which method comprises;
a) providing a sample of a body fluid of an individual;
b) determining a level of CCL3, and/or CCL18 and optionally CCL5 in the sample;
c) comparing the level of CCL3 and/or CCL18 and optionally CCL5 as determined in step b) with a reference level from a sample of a body fluid of a healthy control individual; and
d) screening and/or in vitro diagnosing whether the level of said CCL3 and/or CCL18 and optionally CCL5 as determined in step b) is significantly different from said reference level.

As mentioned above the appropriate chemokine receptor may also be determined, for example by FACS analysis using an antibody, preferably labelled, that specifically recognises the receptor.

Determination of CCL3 and/or CCL18 and optionally CCL5 is carried out as described above, e.g. by using a molecule which specifically recognises the biomarker, e.g. an antibody, an antibody derivative, an antibody fragment, such as e.g. an anti CCL3 or CCL18 antibody, e.g. a commercially available CCL3 or CCL18 specific antibody, e.g. by an immunodiagnostic assay method.

In order to further enhance the sensitivity and/or selectivity of the diagnostic potential of the aforementioned chemokines as biomarkers, the methods described herein may be used in conjunction with assessment of clinical symptoms and/or with the determination of the level of at least one other biomarker in the subject, wherein the amount of the at least one other biomarker may also be indicative of cardiovascular disease or a predisposition thereto. The further biomarker(s) may be selected from other chemokines or cytokines and risk factors that have been indicated as biomarkers of disease, such as CXCL 10 (IP-10), C-Reactive Protein, troponin 1, creatine kinase, creatine kinase MB, CD40L, HDL, ESR, platelet counts, sex, a cardiac index, myoglobin and/or interleukin-6 (preferred embodiment) or any other more or less predictive biomarker of cardiovascular disorders.

In another aspect the present invention provides a method for monitoring the therapeutic efficacy of the treatment of an individual with a substance which is expected to have an effect on reducing or curing an ACS disorder or disease which method comprises determining the level of CCL3 and/or CCL18 and optionally CCL5 or receptor(s) therefor in a sample of a body fluid of said individual and comparing it to the level of CCL3 and/or CCL18 and optionally CCL5 prior to administration of said substance.

In a further aspect, the present invention provides a method for modulating a chemokine response in a vertebrate suffering or predisposed to suffering from an acute cardiovascular syndrome (ACS) comprising the step of increasing or decreasing, or otherwise altering, the functional activity of CCL3 and/or CCL18.

The term "modulating a chemokine" in the context of the present invention also includes within its scope substantially preventing or purposefully inducing in a vertebrate chemokine functional activity.

The term "preventing or purposefully inducing chemokine functional activity" in the context of the present invention includes within its scope increasing or decreasing the expression and/or intracellular or extracellular distribution and/or activity of at least one chemokine as described herein.

Increasing the expression may occur as a result of increasing mRNA expression, or by increasing gene transcription using methods known to those skilled in the art. Those skilled in the art will appreciate that there are many suitable methods to increase or decrease the expression of a nucleic acid sequence encoding a chemokine as herein described.

One skilled in the art will appreciate that the expression or function of one or more chemokines may be increased or decreased by increasing or decreasing the levels of chemokine mRNA respectively by post transcriptional modulation. For example, interfering RNA may be used as a method to decrease chemokine RNA levels.

Increasing or decreasing the intracellular distribution may occur as a result of the addition of chemokine binding proteins to the intracellular environment. Alternatively, the intracellular distribution may be increased, decreased or altered by the addition or removal of signal sequences and/or leader sequences to the chemokine. Techniques used in such procedures will be familiar to those skilled in the art.

Increasing or decreasing the activity of the chemokines can be brought about by bringing the chemokines into contact with inhibitors of chemokines, or activators of chemokines and/or chemokine binding molecules. Examples include antibody, antibody fragment or nanobody; genetically/chemically modified chemokine or chemokine portion with agonistic or antagonistic activity; synthetic small molecular entity; or any other (mammalian, viral or bacterial) protein with CCL3, CCL5 or CCL18 activity modifying capacity. The term "contact" in the context of the present invention means does not require a physical contact. A functional contact, that is where the presence of the inhibitor or activator or chemokine binding protein affects the activity of the chemokine, is sufficient. This may occur when, for example, a third protein mediates the interaction/contact between the chemokine binding molecule and the chemokine. That is, the interaction is indirect.

Suitable inhibitors and activators include but are not limited to inhibitors of chemokine receptors. One skilled in the art will be aware suitable inhibitors or activators. In addition co-factors or chemokine binding molecules may affect their activity. Examples include antibodies and fragments thereof (for example Fab, F(Ab')$_2$, Fv, disulphide linked Fv, scFv, diabody). It will be appreciated that this list is by no means exhaustive.

In a further aspect there is provided a screen for identifying a CCL3 and/or CCL18 modulator for potential use in treating ACS, such as UAP, the screen comprising the steps of:

providing in vitro a cell capable of expressing CCL3 and/or CCL18;

contacting a test modulator molecule with said cell;

subjecting said cell to conditions whereby the cell would normally express CCL3 and/or CCL18 in the absence of the test molecule and;

detecting whether or not the test molecule has a modulatory effect on CCL3 and/or CCL18 activity.

The modulatory effect is preferably an inhibitory effect on CCL3 and/or CCL18 activity and may, for example, refer to expression levels of the mRNA encoding said chemokines, or to protein levels observed. Such levels can easily be determined by the skilled addressee, using techniques well known to the skilled man and as described herein. Typically a control may be run along side, the control comprising a cell to which the test molecule has not been added, in order to obtain a CCL3 and/or CCL18 reference level.

Convenient cells for use in such a method include leukocytes or neutrophils.

According to the above aspects of the invention, advantageously the functional activity of CCL3 and/or CCL18 is modulated using any one of more of the methods selected from the group consisting of: administering a pharmaceutically effective amount of said chemokine/s to the vertebrate; administering a pharmaceutically effective amount of one or more inhibitor/s of said chemokine(s) to the vertebrate; modulating the transcription of said chemokine(s) in the vertebrate; modulating the translation of chemokine(s) in the vertebrate; modulating the post-translational modification of chemokine(s) in the vertebrate and modulating the intracellular or extracellular distribution of said chemokine(s) in the vertebrate.

In a preferred embodiment of this aspect of the invention, the functional activity of said chemokine(s) is modulated by administering a pharmaceutically effective amount of one or more inhibitor/s of said chemokine(s) to the vertebrate. Advantageously, the one or more chemokine inhibitor/s are selected from the group consisting of: chemical chemokine inhibitors, anti-chemokine antibodies and dominant negative mutants of those one or more chemokines described herein.

The functional activity of one or both chemokines may be modulated. One skilled in the art will appreciate that these chemokines may act in isolation or synergistically. In addition there may be functional redundancy in the activity of chemokines.

DETAILED DESCRIPTION OF THE INVENTION

The present invention will now be further described by way of example and with reference to the figures which show:

FIG. 1: Plasma levels of CCL5 and CCL18 as determined by multiplex in stabilised and refractory patients with unstable angina pectoris at t=0 (A). ELISA was used for temporal patterning at t=0, t=2 and t=180 days. CCL5 levels dropped significantly at t=2 and were at the same level at t=180 (B), while CCL18 levels remained elevated at t=2 and dropped back at t=180 (C). Soluble CD40L levels peaked at t=0 and were lowered at t=2 and t=180 (D). CRP levels showed a peak at t=2, and lowered to sub-baseline values (t=0) at t=180 (E). Values represent mean±SEM, *P<0.05, **P<0.001 and N.S.=non-significant.

FIG. 2: Upper quartile plasma levels of CCL5 and CCL18 were significantly associated with the occurrence of refractory ischemic symptoms in unstable angina pectoris, while sCD40L and CRP quartile levels did not show any significant correlation (A). Upper quartile levels of CCL5 at day 0 are predictive for the necessity of future revascularisation procedures (B), while upper quartile levels of CCL18 were predictive for acute coronary syndromes or recurrent symptoms of unstable angina pectoris within the next 18 months (C,D). *P=0.02, **P=0.01, #P<0.01 and N.S.=non-significant.

FIG. 3: Quantitative PCR analysis showed a markedly down-regulated expression of CCL5 and CCL18 in non-stimulated PBMCs of patients with ischemic symptoms at t=0 compared to PBMCs at t=180 (A). In contrast with chemokine receptor surface protein expression in PBMCs, mRNA expression of the CCL5 and CCL18 receptors CCR1, CCR3, CCR4 and CCR5 was also approximately at least 2-fold down-regulated at baseline (B). Values represent mean±SEM, *P<0.05 and **P<0.001.

FIG. 4: Protein expression in PBMCs of CCR3 and CCR5 showed a clear up-regulation of both receptors in CD14$^+$ cells (A,B) and CD3$^{30}$ cells (C,D) at baseline. Triple gating for CD14, CD3 and CCR3/5 revealed the same trend, although CD14$^+$ cells displayed more prominent up-regulation of CCR3 and CCR5 expression than CD3$^+$ cells (E,F). Analysis of total CCR3 and CCR5 surface expression in all PBMCs also showed a dramatic up-regulation of CCR3 and CCR5 expression, indicating that the increase in CCR3 and CCR5 expression is only partly caused by CD3$^+$ and CD14$^+$ positive cells (G,H,I). *P<0.05, **P<0.01 and #P<0.001.

FIG. 5: Stimulation of PBMCs for 6 hours with rCCL5 and sCCL18 showed no significant differences in CCR1 (A), CCR4 (C) and CCR5 (D) mRNA expression. CCR3 expression was markedly down-regulated after stimulation with sCCL18, but not with rCCL5 (B). Values represent mean±SEM, *P<0.01, N.S.=non-significant, rCCL5=recombinant CCL5, sCCL18=synthetic CCL18.

FIG. 6: Assessment of heterophilic interaction between CCL5 and CCL18 on PAGE (18%). Lanes 1 and 2 show reference mobility of rCCL5 (7,851 kDa) and sCCL18 (7,855 kDa), both chemokines showed a poor tendency to form 15.6 kDa homodimers. Lanes 3 and 4 were loaded with mixtures of rCCL5 and sCCL18 in a 1:1 and 1:5 ratio (weight:weight), at which dimers have been crosslinked by incubation for 30 min at RT with 25 mM paraformaldehyde. Note the slightly higher electrophoretic mobility and slightly more yellowish staining of CCL18 monomer and dimer. The extent of dimer formation was not altered after co-incubation and subsequent crosslinking of CCL5 and CCL18, indicating that CCL5 and CCL18 are probably not engaged in any significant heterophilic crossinteraction even at supra-physiological concentrations. The total protein load per lane was constant (2 µg) (A).

FIG. 7: The PAGE analysis was corroborated by MALDI-TOF MS analysis: CCL5 and CCL18 (10 pmol/µl) gave mass peaks at approximately 7,860 Da (M$^+$; theoretical mass of CCL5 and CCL18 7,851 and 7,855 Da, respectively), with only minor peaks at approximately 15,730 Da, illustrating the low tendency to form homodimers (M$_2^+$) (A,B). MALDI-TOF mass spectrometry of CCL18 that had been pre-incubated with CCL5 at a 1:1 and 1:5 w:w ratio (total concentration 10 pmol/µl) in 50 mM HEPES/0.1 mM EDTA with paraformaldehyde gave an essentially similar pattern and dimer formation was equally marginal at both ratios (C,D).

FIG. 8: Total levels of CD 14$^+$ cells (monocytes and neutrophils) did not differ between t=0 and t=180, whereas CD3$^+$ cells showed a small (11.8%), albeit significant decrease at baseline (A). At the mRNA level, an increase of HNP-3+ neutrophils was observed, suggestive of enhanced post-ischemic neutrophil release However, the CCR2:CX3CR1 expression ratio, a measure of monocyte subset profile, was not differentially regulated (B). Values represent mean±SEM, *P=0.01, **P<0.001 and N.S.=non-significant.

FIG. 9: Demonstrates that a transient exposure of mice to elevated levels of CCL18 in the circulation (as effected by repeated administration of recombinant CCL18 protein) will aggravate the development of atherosclerosis and thereby enhance the risk of cardiovascular disease FIG. 10: Demonstrates that atherosclerotic plaque development in the aortic sinus of hyperlimidemic (LDLr−/−) mice with a deficiency of CCL3 is sharply reduced.

FIG. 11: Circulating CCL3 levels in APRAIS were comparable with those seen in patients from the MISSION! cohort (A). Temporal CCL3 monitoring clearly shows the transient increase of CCL3 during ischemia, since levels were significantly lowered at t=180 compared to t=0 (B). *P=0.03 and **P<0.001.

FIG. 12: Upper quartile levels of CCL3 at baseline are predictive for the occurrence of acute coronary syndromes during follow-up (A). Furthermore, upper quartile levels were also indicative of recurrent ischemic symptoms during or directly after hospitalisation (B). *P=0.01 and **P<0.01.

FIG. 13: Plasma levels of CCL3 (A), CCL5 (B) and CXCL8 (C) were significantly elevated in AMI patients (●) versus controls (○), whereas CXCL10 (D) showed the opposite pattern. *P=0.025, P=0.006, *P=0.02 and #P=0.004.

FIG. 14: Assessment of IL-6, CCL3 and CXCL10 levels in LAD ligated or sham operated mice. Cardiac ischemia induced significantly elevated levels of IL-6, and CCL3, (A,B). On the other hand, CXCL10 displayed an inversed pattern (C). *P=0.007, P=0.02, and *P=0.03.

FIG. 15: Ligated mice displayed a significant increase in the percentage of circulating T-cells with a concomitant enrichment in the CCR5+ and CXCR3+ subsets (A-C). The increase in circulating T-cells was accompanied by a decrease in CCR5+ splenic T-cells, whereas no effects on total or CXCR3+ splenic T-cells was apparent (D-F). *P=0.04, P-0.02, *P=0.04 and P=0.004.

Figure 18:
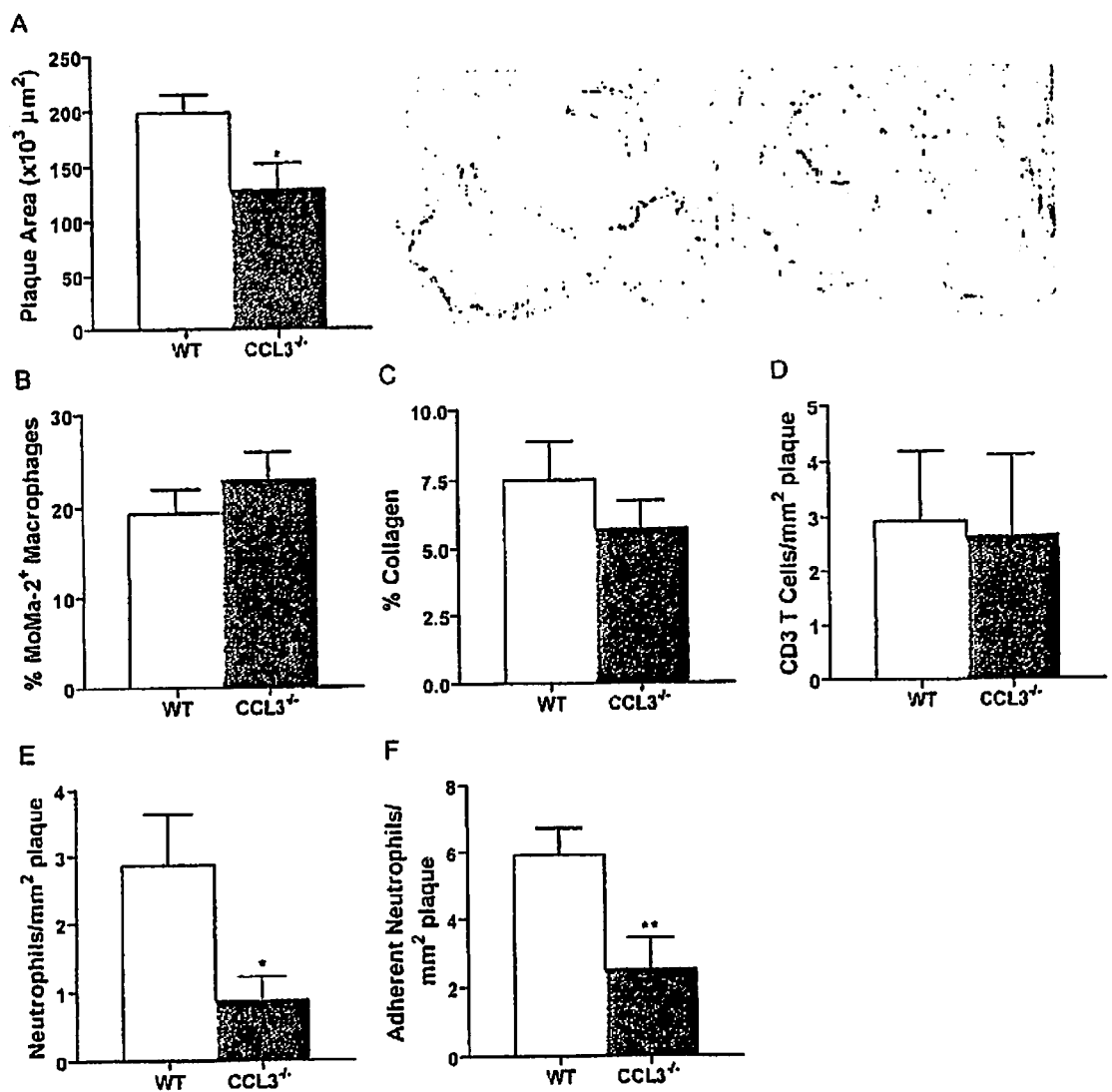

FIG. 18 shows atherosclerotic lesions were significantly smaller in CCL3$^{-/-}$ chimeras compared to WT controls (A with representative pictures). Macrophages (B), collagen (C) and T cell content (D) was similar between WT and CCL3$^{-/-}$ chimeras. Neutrophil influx (E) and adhesion (F) was significantly attenuated in CCL3$^{-/-}$ chimeras. Black bars represent WT controls and white bars CCL3$^{-/-}$ chimeras. *p<0.05, **p<0.01.

Figure 19:
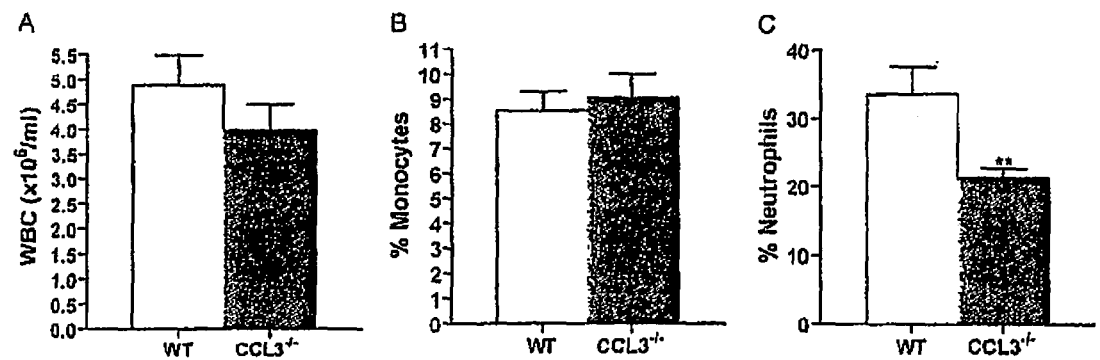

FIG. 19 shows total number of white blood cells (A) and monocytes (B) was not different in CCL3−/− mice, whereas neutrophil numbers (C) were significantly decreased. Black bars represent WT and white bars CCL3$^{-/-}$ chimeras. p<0.01, *p<0.001.

Figure 20:
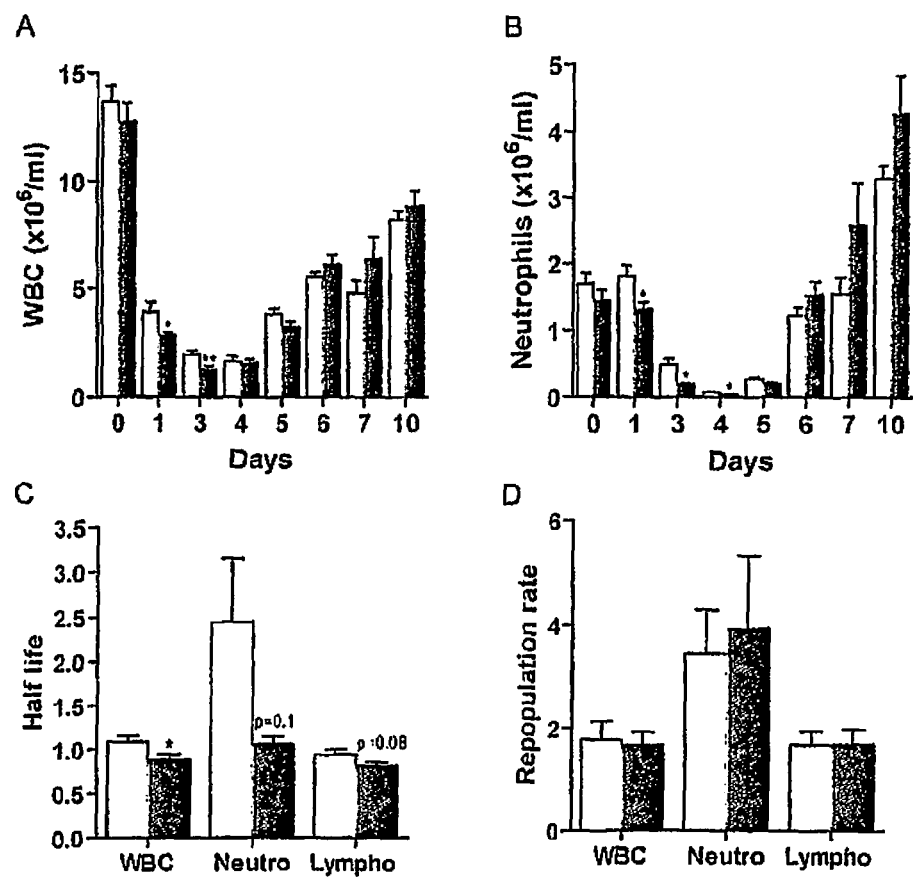

FIG. 20 shows kinetics of cyclophosphamide induced transient leukopenia (A) and neutropenia (B) in control (white bars) and CCL3$^{-/-}$ mice (black bars). Elimination of neutrophils is accelerated in in CCL3$^{-/-}$ chimeras (C), while repopulation is similar (D). Black bars represent WT mice and white bars represent CCL3$^{-/-}$ mice. *p<0.05. **p<0.01.

Figure 21:
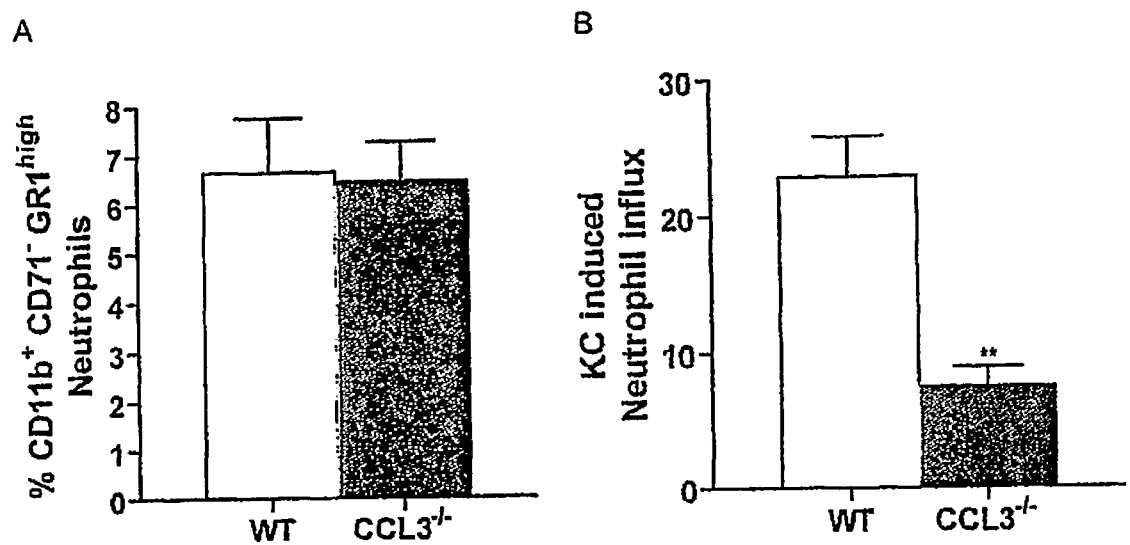

FIG. 21 shows intra peritoneal injection of KC did not affect circulating CD11b$^+$ CD71$^-$ $^{Gr}$1$^{high}$ neutrophil numbers in WT and CCL3$^{-/-}$ mice (A). KC elicited induction of neutrophil influx to the peritoneal cavity was ≈2.5 times lower in CCL3$^{-/-}$ mice compared to WT mice (B). Black bars represent WT mice and white bars represent CCL3$^{-/-}$ mice. **p=0.003,

EXAMPLE 1

CCL5 (RANTES) and CCL18 (PARC) are specific markers of refractory unstable angina pectoris and are transiently raised during severe ischemic symptoms.

Methods

Study Population

All chemokines and inflammatory parameters were determined in plasma samples of a patient cohort, derived from the well defined APRAIS (Acute Phase Reaction and Ischemic Syndromes) study[13]. In brief, 54 patients who were admitted to the emergency department of the Leiden University Medical Center between March and September 1995 with unstable angina pectoris Braunwald class IIIB were included and followed for up to 18 months. Venous blood samples were obtained on admission (t=0) after 2 (t=2) and 180 days after admission (t=180), centrifuged and plasma aliquots were stored at −80° C. until further analysis. All patients had received standard medical therapy, i.e. aspirin 300 mg orally, nitro-glycerine intravenously and heparin infusion based titrated to the activated partial thromboplastin time. A clinical end point of the APRAIS study was the occurrence of refractory unstable angina pectoris during hospitalisation. Unstable angina pectoris was considered refractory if angina at rest, despite medical treatment, remained or re-occurred, prompting invasive coronary assessment and subsequent revascularization therapy. Although the study cohort was relatively small, it constituted a clearly defined, well documented population with a similar starting point. All subjects gave written informed consent and the study protocol was approved by the Ethics Committee of the Leiden University Medical Center.

Isolation of Cells

PBMCs from patients (t=0 and t=180) as well as from 6 healthy age matched volunteers were isolated from venous EDTA blood samples through density centrifugation on Histopaque (Sigma, St. Louis, Mo.). PBMCs were collected from the interphase and washed twice with culture medium, consisting of Iscove's modified Dulbecco's medium containing glutamax (Gibco, Paisly, UK) and supplemented with 10% FCS. PBMCs were cryopreserved in culture medium containing 20% FCS and 10% dimethylsulfoxide until further use.

Multiplex Chemokine Assay

Circulating levels of the chemokines CCL2, CCL3, CCL5, CCL11, CCL17, CCL18, CCL22, CXCL8, CXCL9, CXCL10 and the chemokine like factor MIF, the cytokines OSM, IFN-γ and OPG and adhesion molecules sRank1, sVCAM and sICAM were determined in t=0 samples with a custom made multiplex bio-assay using the Bio-Plex Suspension Array system (Bio-Rad laboratories, Hercules, Calif.) Plasma samples were filtered and subsequently diluted with 10% normal rat and mouse serum (Rockland, Gilvertsville, Pa.) to block residual non-specific antibody binding. 1000 microspheres were added per chemokine (10 µl/well) in a total volume of 60 μl, together with standard and blank samples, and the suspension incubated for 1 hour in a 96 well filter plate at room temperature (RT). Then, 10 μl of biotinylated antibody mix (16.5 μg/ml) was added and incubated for 1 hour at RT. After washing with PBS-1% BSA-0.5% Tween 20, beads were incubated with 50 ng/well streptavidin R-phycoerythrin (BD Biosciences, San Diego, Calif.) for 10 minutes. Finally, beads were washed again with PBS-1% BSA-0.5% Tween 20, and the fluorescence intensity was measured in a final volume of 100 μl high-performance ELISA buffer (Sanquin, Amsterdam, the Netherlands). Measurements and data analysis were performed with the Bio-Plex Suspension Array system in combination with the Bio-Plex Manager software version 3.0 (Bio-Rad laboratories, Hercules, Calif.) (see also ref. No: 14)

ELISA and Other Assays

For temporal analysis of human CCL5 and CCL18 plasma levels during follow up, the t=0, t=2 and t=180 samples were assayed by a CCL5 instant ELISA kit (Bender MedSystems, Vienna, Austria) and a CCL18 ELISA (RayBiotech, Norcross, Ga.), respectively, according to manufacturers protocol. Baseline inflammatory parameters such as C-reactive protein, fibrinogen, erythrocyte sedimentation rate (ESR) and plasminogen activator inhibitor 1 (PAI-1) were determined as described in detail previously[13]. Soluble CD40 ligand (sCD40L) and Interleukin 6 (IL-6) were determined via a highly sensitive immunoassay (Quantakine HS, R&D Systems, Minneapolis, Minn.), t=180 CRP samples via a turbidimetric assay on a fully automated Modular P800 unit (Roche, Almere, the Netherlands).

Assessment of Heterophilic CCL5 and CCL18 Interaction

Sodium Dodecyl Sulfate-Polyacrylamide Gel Electrophoresis (SDS-PAGE) was used to assess whether recombinant CCL5 (7.8 kDa) and synthetic CCL18 (7.8 kDa) engage in heterophilic interactions. Proteins (rCCL5, sCC118, rCCL5/sCCL18 at a 1:1 and a 1:5 weight ratio (w:w); 2 μg total protein per lane) were incubated for one hour at RT in 50 mM HEPES/0.1 mM EDTA buffer (pH=7.4), after which 25 mM of paraformaldehyde was added to cross link any formed homo- or heterodimers. After 30 minutes, protein mixtures were denatured in loading buffer and subjected to SDS-PAGE (18%; 2 μg protein per lane, one hour at 70 mV and 30 minutes at 150 mV), proteins were visualized by silver staining. Protein mixtures were also analysed on a Voyager-DE Pro MALDI-TOF mass spectrometer (PerSeptive Biosystems, Framingham, Mass.).

RT-PCR Analyses

To assess expression of CCL5, CCL18, CCR1, CCR2, CCR3, CCR4, CCR5, CX3CR1 and human neutrophil peptide-3 (HNP-3) in PBMCs, mRNA was isolated and analyzed. Guanidium thiocyanate-phenol was used to extract total RNA from PBMCs, samples were subjected to DNAse I treatment (Promega, Madison, Wis.) after which cDNA was generated using RevertAid M-MuLV reverse transcriptase (Fermentas, Burlington, Canada) according to manufacturer's protocol[2]. Semi quantitative gene expression was performed using the SYBR-Green method (Eurogentec, Liege, Belgium) on an ABI PRISM 7700 machine (Applied Biosystems, Foster City, Calif.) with primers for CCL5, CCL18, CCR1, CCR2, CCR3, CCR4, CCR5, CX3CR1, CD11b and human neutrophil peptide-3 (HNP-3). Cyclophilin and Hypoxanthine Guanine Phosphoribosyl Transferase (HPRT) were used as housekeeping genes (see Table 1 for primer sequences).

TABLE 1

Primer sequences used for RT-PCR analysis.

| Gene name | Forward | Reverse |
|---|---|---|
| HPRT | GAAATGTCAGTTGCTGCATTCCT | ACAATCCGCCCAAAGGGAAC |
| Cyclo-philin | AGTCTTGGCAGTGCAGATGAA | GAAGATGAGAACTTCATCCTAAAGCATA |
| CCR1 | TCCTGCTGACGATTGACAGGTA | GTGCCCGCAAGGCAAAC |
| CCR2 | TTCGGCCTGAGTAACTGTGAAA | TGAGTCATCCCAAGAGTCTCTGTC |
| CCR3 | CTGCTGCATGAACCCGGT | GGAAGAAGTGGCGAGGTACT |
| CCR4 | ACTGTGGGCTCCTCCAAATTT | TCCATGGTGGACTGCGTG |
| CCR5 | AGACATCCGTTCCCCTACAAGAA | CAGGGCTCCGATGTATAATAATTGA |
| CX3CR1 | GTCCACGTTGATTTCTCCTCATC | CGTGTGGTAAGTAAAATTGCTGCT |
| HNP-3 | CCCAGAAGTGGTTGTTTCCCT | TTTCCTTGAGCCTGGATGCT |
| CCL5 | TCTGCGCTCCTGCATCTG | CAGTGGGCGGGCAATG |
| CCL18 | CCTGGAGGCCACCTCTTCTAA | TGCAGCTCAACAATAGAAATCAATT |

Relative gene expression was calculated by subtracting the threshold cycle number (Ct) of the target gene from the average Ct of Cyclophiline and HPRT and raising two to the power of this difference.

Flow Cytometry

CCR3 and CCR5 surface expression on CD3[+] and CD 14[+] PBMCs was assessed by flow cytometry. Cryopreserved PBMCs were thawed, washed three times in RPMI 1640 containing 20% FCS and subsequently stained using APC conjugated anti-CD3 and anti-CD14 antibodies (BD Biosciences, San Jose, Calif.) as well as FITC conjugated anti-CCR3 and anti-CCR5 antibodies (R&D Systems). Non-specific isotypes FITC conjugated Rat IgG2a and FITC conjugated mouse IgG2b antibodies (eBiosciences, San Diego, Calif.) were used as negative controls. Samples were analysed with a fluorescence activated flow cytometer (FACSCalibur) and subsequently analyzed using CELLQuest software (BD Biosciences), 50,000 cells were counted for each sample.

PBMC Stimulation Assay

Cryopreserved PBMC specimens, obtained from six healthy volunteers were thawed as described above, plated in a U-shaped round bottom 96-well plate (Greiner Bio-one) and stimulated for 6 hours at 37° C. with plain medium (control) or medium supplemented with 50 ng/ml recombinant CCL5 (Peprotech, Rocky Hill, N.J.), 50 ng/ml of the synthetic CCL18 peptide SM-1 (sCCL18), or a combination of rCCL5 and sCCL18 (25 ng/ml per peptide)[3]. After incubation, total RNA was isolated from the cells, cDNA was prepared and chemokine receptor expression was determined.

Statistical Analysis

Differences between our study populations and the original cohort were examined by Fisher's exact test and Student's unpaired t-test. Plasma levels of chemokines and inflammatory markers were tested for normal Gaussian distribution and values were log-transformed in the case of a skewed distribution when appropriate. Regarding the latter, geometric instead of arithmetic means are given. Means were compared by unpaired two-tailed Student's t-test or Mann-Whitney U-test when appropriate. In order to assess the predictive value of CCL5 and CCL18 for the occurrence of refractory symptoms, independent of potentially confounding factors, a multivariate analysis was performed, correcting for age, HDL and ESR levels, as well as for other established cardiovascular risk factors (e.g. hypertension, hypercholesterolemia, use of lipid and blood pressure lowering medication, diabetes mellitus, smoking behaviour, BMI and history of cardiovascular disease) and biomarkers sCD40L and CRP. Quartile distribution was assessed and used for Spearman's correlation coefficient and Pearson's chi-square testing to determine the association of chemokine plasma levels as well as levels of sCD40L and CRP for the occurrence of refractory UAP. Receiver operating characteristics curves were generated to assess predictive value of chemokines for refractory ischemic symptoms. Correlation analysis between multiplex and ELISA values and between chemokines and inflammatory parameters were performed by Spearman's rank correlation test. FACS results were analysed via paired t-test, the stimulation assay was analysed via ANOVA. A two-sided p-value<0.05 was considered significant. All analyses were performed using SPSS version 14.0 software (SPSS, Chicago, Ill.).

Results

Study Population

Plasma analyses on chemokines were performed in a subcohort of previously unfrozen plasma samples of 54 consecutive patients, excluding selection bias. This subcohort, consisting of 31 patients with stabilised and 23 with refractory ischemic symptoms, matched with the original cohort on cardiovascular risk factors, history of myocardial infarction or PTCA/CABG and laboratory parameters (Tables 2A and B).

TABLE 2A

Baseline patient characteristics and laboratory parameters.

| | Chemokine cohort (N = 54) | APRAIS (N = 211) | P-value |
|---|---|---|---|
| Age, years | 65.4 ± 11.0 | 62.7 ± 10.2 | 0.08 |
| Refractory (%) | 43 | 36 | 0.43 |
| Male gender (%) | 73.8 | 71.1 | 0.75 |
| Current smoker (%) | 24.6 | 30.5 | 0.45 |
| BMI (kg/m$^2$) | 25.2 ± 6.0 | 25.9 ± 3.36 | 0.23 |
| Diabetes (%) | 16.4 | 14.6 | 0.98 |
| Hypertension (%) | 23 | 23.5 | 0.99 |
| Statin use (%) | 8.2 | 12.2 | 0.48 |
| History of: | | | |
| Myocardial infarction (%) | 45 | 43.2 | 0.88 |
| PTCA (%) | 26 | 29.1 | 0.75 |
| CABG (%) | 23 | 21.6 | 0.86 |
| Laboratory parameters: | | | |
| Total cholesterol, mmol/l | 6.00 ± 1.5 | 6.18 ± 1.2 | 0.38 |
| HDL, mmol/l | 1.14 ± 0.4 | 1.14 ± 0.3 | 0.97 |
| CRP, mg/l * | 2.36 | 2.66 | 0.50 |
| ESR, mm/hr * | 16.44 | 14.88 | 0.30 |
| Fibrinogen, g/l * | 3.56 | 3.42 | 0.34 |

TABLE 2B

Chemokine cohort baseline patient characteristics and laboratory parameters

| | Stabilised (N = 31) | Refractory (N = 23) | P-value |
|---|---|---|---|
| Age, years | 67.3 ± 10.2 | 64.5 ± 11.4 | 0.30 |
| Male gender (%) | 87 | 63 | 0.05 |
| Current smoker (%) | 22 | 25 | 0.69 |
| BMI (kg/m$^2$) | 24.9 | 26.7 | 0.78 |
| Diabetes (%) | 9 | 19 | 0.16 |
| Hypertension (%) | 17 | 38 | 0.39 |
| History of: | | | |
| Myocardial infarction (%) | 48 | 47 | 0.89 |
| PTCA (%) | 30 | 25 | 0.57 |
| CABG (%) | 35 | 16 | 0.19 |
| Laboratory parameters: | | | |
| Hemoglobine, mmol/l | 8.27 ± 2.1 | 8.51 ± 0.8 | 0.61 |
| Hematocrite (%) | 47 | 41 | 0.26 |
| Leucocytes, 10$^9$/l | 7.49 ± 2.9 | 7.68 ± 2.2 | 0.79 |
| Platelet count, 10$^6$/l | 186.5 ± 66 | 223.9 ± 75 | 0.07 |
| Glucose, mmol/l | 7.37 ± 2.7 | 6.49 ± 1.4 | 0.15 |
| Creatinine, μmol/l | 99.2 ± 52.3 | 108.7 ± 32.1 | 0.44 |
| Cholesterol, mmol/l | 5.92 ± 1.8 | 6.16 ± 1.0 | 0.56 |
| HDL, mmol/l | 1.23 ± 0.4 | 0.99 ± 0.2 | 0.02 |
| ESR, mm/hr * | 14.15 | 20.70 | 0.03 |
| Fibrinogen, g/l * | 3.42 | 3.78 | 0.26 |
| CRP, mg/l * | 2.14 | 2.77 | 0.47 |
| sCD40L, pg/ml | 23.6 | 20.3 | 0.32 |

As not all 54 patients responded to donate blood after 180 days, ELISA analysis at this point was performed for 47 patients (stabilised 29 vs. refractory 18), but the baseline characteristics of this subcohort matched with that of the original cohort (data not shown). Comparison for baseline demographics in the chemokine cohort showed no striking differences between refractory versus stabilised patients, except for a small, but significant difference in gender composition (87% vs. 67% males; P=0.05); the mean age of all patients was 65 years (41 to 85 years). Regarding the clinical and plasma lipid parameters at baseline, total cholesterol levels in stabilized and refractory patients did not differ (5.92 vs. 6.16 mmol/l; P=0.56), whereas HDL levels were lower (1.23 vs. 0.99 mmol/l; P=0.02) in the latter population. This group also displayed an increased tendency towards a higher inflammatory status, as illustrated by elevated levels of the ESR (14.15 vs. 20.7 mm/hr; P=0.03) albeit that fibrinogen and CRP levels were essentially similar. No differences were observed in baseline sCD40L levels between groups.

Multiplex Analysis: Upregulation of CCL5 and CCL18

All of the chemokine and cytokine data as determined by multiplex analysis (t=0 samples) were log-transformed before further statistical analysis because of their skewed distribution profiles, except for OPG. Plasma levels of the majority of chemokines and cytokines did not differ between stabilized and refractory patients. CCL5 (23.1 vs. 32.7 ng/ml; P=0.018) and CCL18 levels (53.7 vs. 104.4 ng/ml; P=0.011) however appeared to be significantly increased in refractory patients, while there was a borderline significant increase in those of CCL3 (53.6 vs. 73.7 pg/ml; P=0.09) (Table 3 and FIG. 1A).

TABLE 3

Chemokine plasma concentrations analysed via the multiplex technique.

| Variable | Stabilised | Refractory | P-value |
|---|---|---|---|
| CCL5, pg/ml | 23158 | 32704 | 0.018 |
| CCL18, pg/ml | 53678 | 104399 | 0.011 |
| CCL2, pg/ml | 154 | 146 | 0.77 |
| CCL3, pg/ml | 53.6 | 73.7 | 0.09 |
| CCL11, pg/ml | 63.7 | 65.8 | 0.88 |
| CCL17, pg/ml | 40.3 | 51.2 | 0.34 |
| CCL22, pg/ml | 527 | 546 | 0.79 |
| CXCL8, pg/ml | 12.4 | 13.4 | 0.84 |
| CXCL9, pg/ml | 158 | 156 | 0.96 |
| CXCL10, pg/ml | 221 | 157 | 0.12 |
| MIF, pg/ml | 330 | 439 | 0.45 |
| OPG, pg/ml* | 937 | 1096 | 0.25 |
| OSM, pg/ml | 456 | 690 | 0.25 |
| sRankL, pg/ml | 5.0 | 5.7 | 0.83 |
| sVCAM , pg/ml | 681082 | 735190 | 0.45 |
| sICAM, pg/ml | 106340 | 117625 | 0.28 |

Values are geometric means
*denotes arithmetic mean

Figure 6:
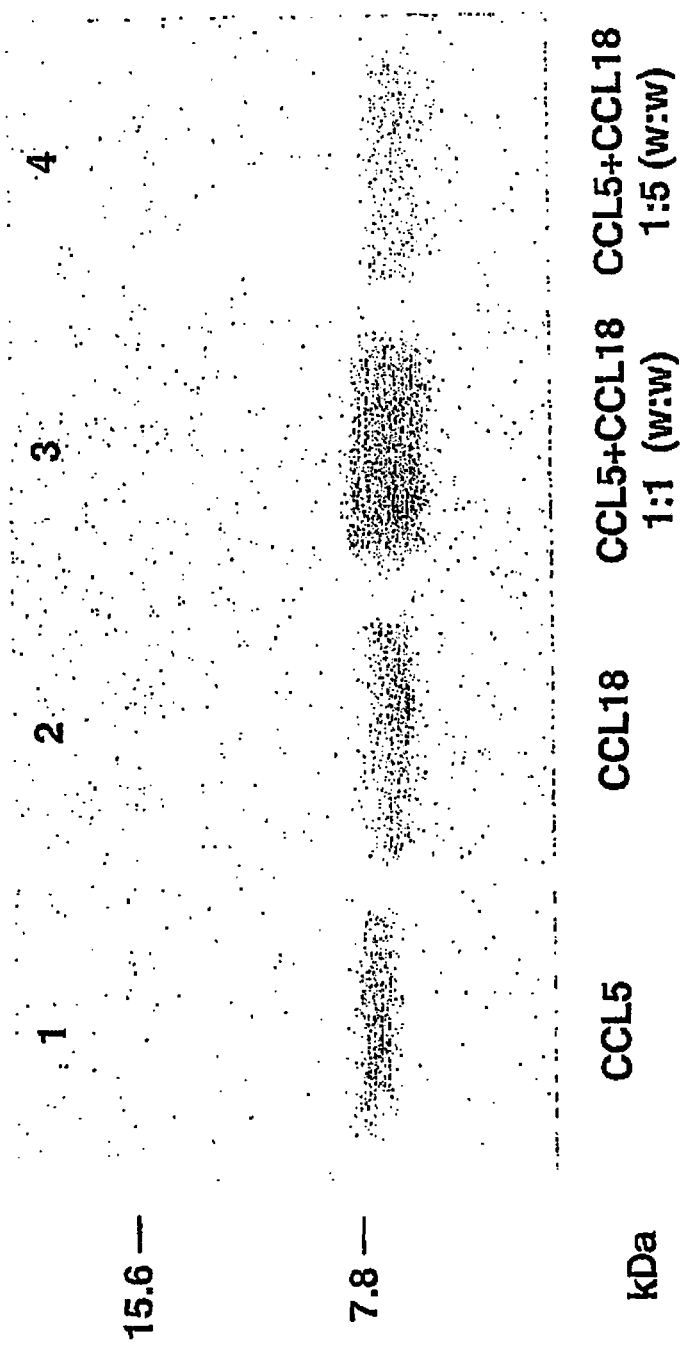
Figure 7:
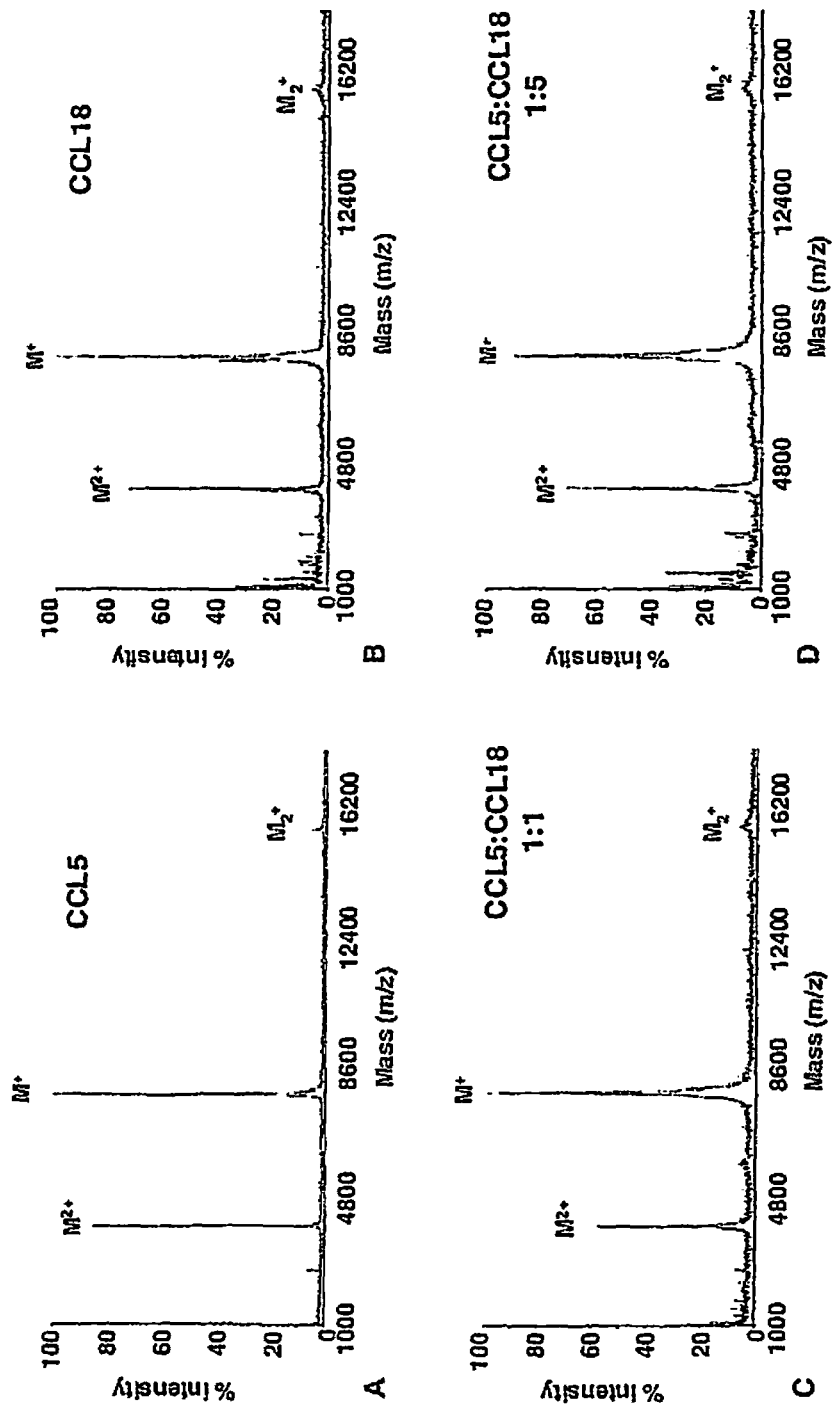

Moreover, the observed differences in CCL5 levels remained significant after multivariate analysis adjusting for cardiovascular risk factors and sCD40L and CRP levels (P=0.023), whereas CCL18 levels were borderline significant (P=0.06). However, differences in CCL 18 levels reached significance after multivariate analysis for all confounding factors but HDL (P=0.021). Therefore, CCL5 as well as CCL18 seem to be independent predictors of the occurrence of refractory ischemic symptoms, even when adjusting for sCD40L and CRP levels. Furthermore, CCL5 and CCL18 levels showed no mutual correlation (R=0.05; P=0.7), reflecting that these chemokines are regulated or operate in an independent manner. Still, although no significant heterophilic interactions between CCL5 and CCL18 were observed, it is conceivable that both chemokines, sharing CCR3 as common target receptor will interact functionally (FIGS. 6 and 7). CXCL10 had a tendency to rise in stabilised patients, although not quite significant (221.6 vs. 157.5 pg/ml; P=0.12), which could point towards a protective effect of this specific chemokine. Levels of IFN-γ were merely undetectable and are therefore not shown.

Next, we sought to assess if CCL5 and CCL18 levels have diagnostic potential. Given the cohort size, levels of CCL5 and CCL18 were categorized into quartiles and analyzed for correlation with the occurrence of future refractory ischemic symptoms (Table 4A).

TABLE 4A

CCL5 and CCL18 quartile levels at baseline as determined by multiplex analysis

| Quartiles | CCL5 | CCL18 |
|---|---|---|
| 1 | <15.1 | <39.3 |
| 2 | >15.1 and <25.5 | >39.3 and <66.0 |
| 3 | >25.5 and <40.3 | >66.0 and <130.0 |
| 4 | >40.3 | >130.0 |

All values are in ng/ml

Figure 2:
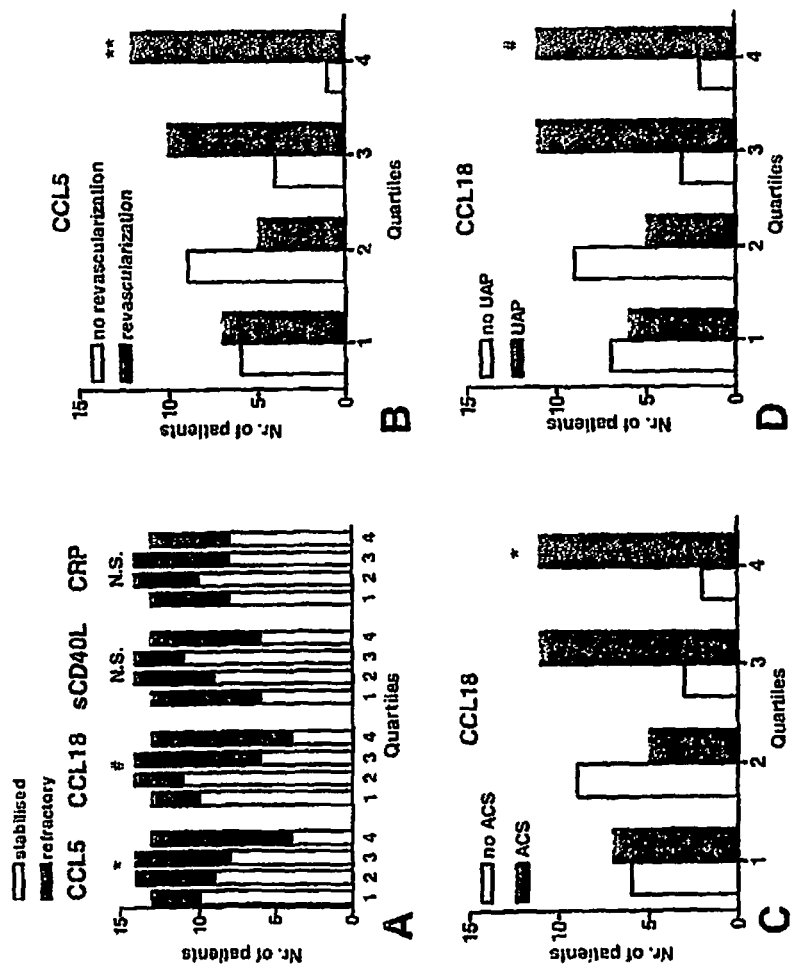

The risk of refractory ischemic symptoms was seen to be increased in the upper quartiles of CCL5 (R=0.32; P=0.017; Linear-by-linear association chi-square 5.53; P=0.019), while this trend was even more pronounced for CCL18 (R=0.392; P=0.003; linear-by-linear association chi-square 8.105; P=0.004) (FIG. 2A). Elevated CCL18 levels were slightly more predictive than those of CCL5 as indicated by the receiver operating characteristics curve (area under the curve 0.71 vs. 0.69). Cut-off values of >40 ng/ml for CCL5 and >130 ng/ml for CCL18 yielded a sensitivity of 73.9% and 65.2%, respectively as well as a specificity of 67.7% and 61.3%. Combined analysis of the upper two quartiles of CCL5 and CCL18 for the occurrence of refractory ischemic symptoms revealed a very significant relation ($\chi^2$ with continuity correction 8.12; P<0.01). While the sensitivity reached 47.8%, the specificity of the combined analysis was a remarkably high 90.3%. The positive predictive value of combined analysis for CCL5 and CCL18 levels was 78.5% with a concomitant negative predictive value of 70.0%. Adding sCD40L or CRP levels to the analysis did not yield any further increase in sensitivity, specificity or predictive value (data not shown).

CCL5 and CCL18 ELISA Verification and Follow-Up Analysis

Figure 1:
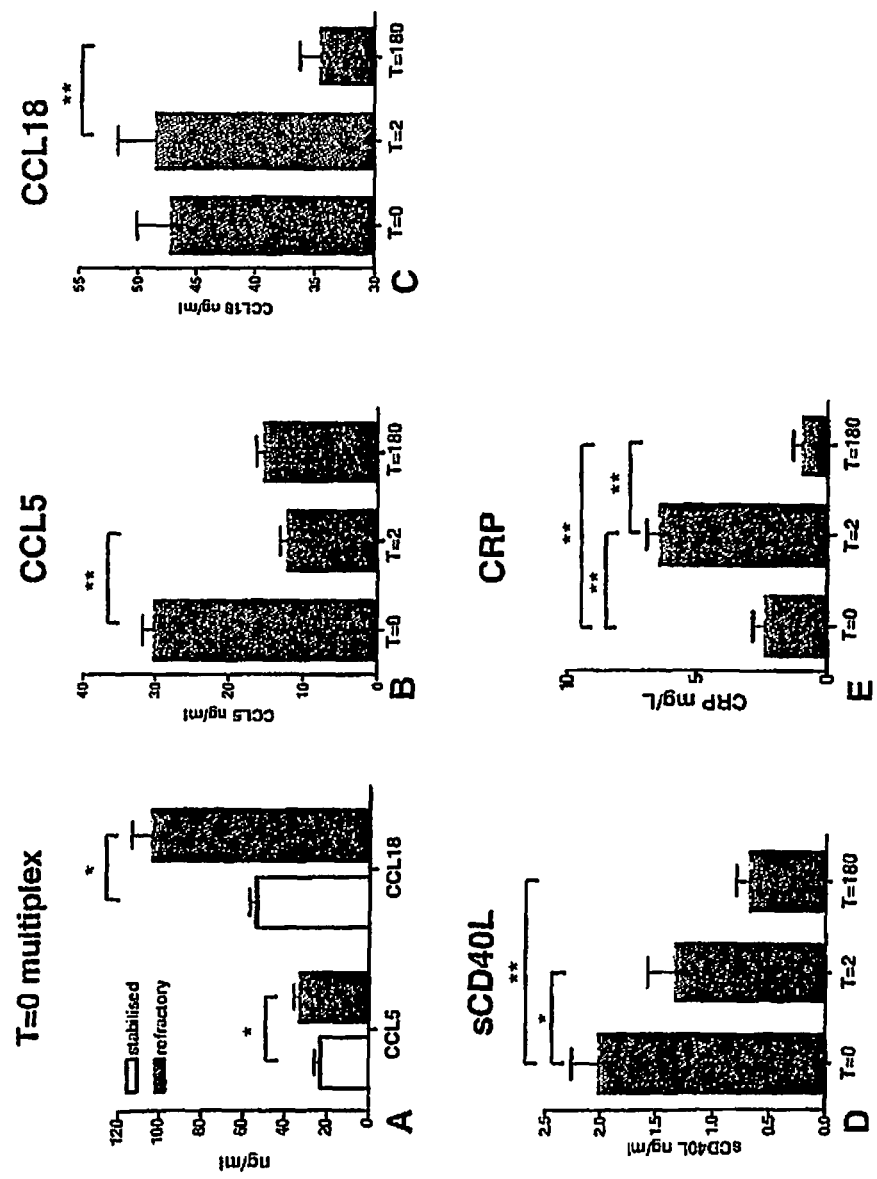

Mean and individual ELISA and multiplex CCL5 levels corresponded excellently (P<0.001). Moreover, CCL5 plasma levels were also seen to be increased in refractory compared to stabilised patients at day 0 when assessed by ELISA (36.4 vs. 26.5 ng/ml). Interestingly, already after two days, a marked decrease in plasma CCL5 levels was observed in the whole cohort (12.1 versus 30.3 ng/ml; P<0.001) and reduced CCL5 levels were also observed at t=180, showing that CCL5 is transiently raised during an episode of unstable angina pectoris (FIG. 1B). We did not observe any differences between the stabilized and refractory groups at 2 and 180 days post inclusion. Plasma levels of CCL18 showed a different temporal pattern after ischemic symptoms. ELISA analysis confirmed the differential expression of CCL18 at day 0 between refractory and stabilised patients (56.2 vs. 41.1 ng/ml; P=0.02). Although absolute values were slightly lower in the ELISA compared to the multiplex assay, statistical analysis revealed an excellent correlation between the two assays (Spearman's test; P<0.001). Interestingly, CCL18 levels of the total cohort at day 2 did not differ with the baseline levels (day 0), suggesting that CCL18 and CCL5 levels might be regulated via separate mechanisms. At 180 days, CCL18 levels were significantly down-regulated compared the day 2 values (48.4 vs. 34.5 ng/ml; P<0.001), suggestive of a role of CCL18 in cardiac ischemia-reperfusion related processes (FIG. 1C).

Soluble CD40 Ligand and CRP

Levels of both sCD40L as well as CRP were significantly elevated at t=0 compared to t=180 (sCD40L 2.04 vs. 0.69 ng/ml; P<0.001, CRP 2.36 vs. 0.96 mg/l; P<0.001) (FIG. 1D,E). However, sCD40L levels started to decline already at t=2 (1.35 ng/ml; P<0.05) indicating that elevated levels at baseline reflect a platelet activation related acute phase response. As soluble CD40L t=0 and t=2 levels at correlated significantly with CCL5 t=0 and t=2 levels (t=0 R=0.40; P<0.01, t=2 R=0.35; P=0.01), elevated CCL5 levels may be primarily caused by platelet activation as well. sCD40L however showed a significant negative correlation with CCL18 levels at t=0 (R=−0.36; P=0.01), suggesting that latter represent a feedback response to platelet activation. CRP levels were even further increased at t=2 (6.43 mg/l; P<0.001) which is in keeping with previous reports[15,16], and presumably indicative of an enhanced post-ischemic systemic inflammatory status in these patients two days after ischemia and/or coronary intervention. CRP levels showed no correlations with CCL5 or CCL18 levels. Quartile levels of sCD40L as well as CRP did not have any potential to predict refractory ischemic symptoms (R=0.043 and R=−0.034; N.S) (FIG. 2A: for quartile distribution, see Table 4B).

TABLE 2B

CRP and sCD40L quartile levels at baseline.

| Quartiles | CRP mg/L | sCD40L ng/ml |
|---|---|---|
| 1 | <1.2 | <14.2 |
| 2 | >1.2 and <2.6 | >14.2 and <26.4 |
| 3 | >2.6 and <6.5 | >26.4 and <33.7 |
| 4 | >6.5 | >33.7 |

All values are in ng/ml

Inflammation and Clinical Follow-Up

Correlation analysis for all chemokines with systemic inflammatory parameters fibrinogen, IL-6, PAI-1 and ESR revealed no association, except for a weak correlation between CXCL10 and IL-6 levels (R=0.29; P=0.02, other data not shown). Importantly, the baseline upper quartile levels of CCL5 as determined by multiplex were seen to correlate with the need for revascularization procedures within the next 18 months (R=0.35; P=0.01). Furthermore, baseline upper quartile levels of CCL18 correlated with the re-occurrence of unstable angina pectoris (UAP) during hospitalisation (R=0.36; P=0.007) as well as with the occurrence of an acute coronary syndrome (ACS) during the 18-month period of follow-up (R=0.31; P=0.02)(FIGS. 2B-D). Baseline levels of sCD40L and CRP did not correlate with any of the follow-up parameters (data not shown).

PBMC Chemokine and Chemokine Receptor Expression Analysis

Figure 3:
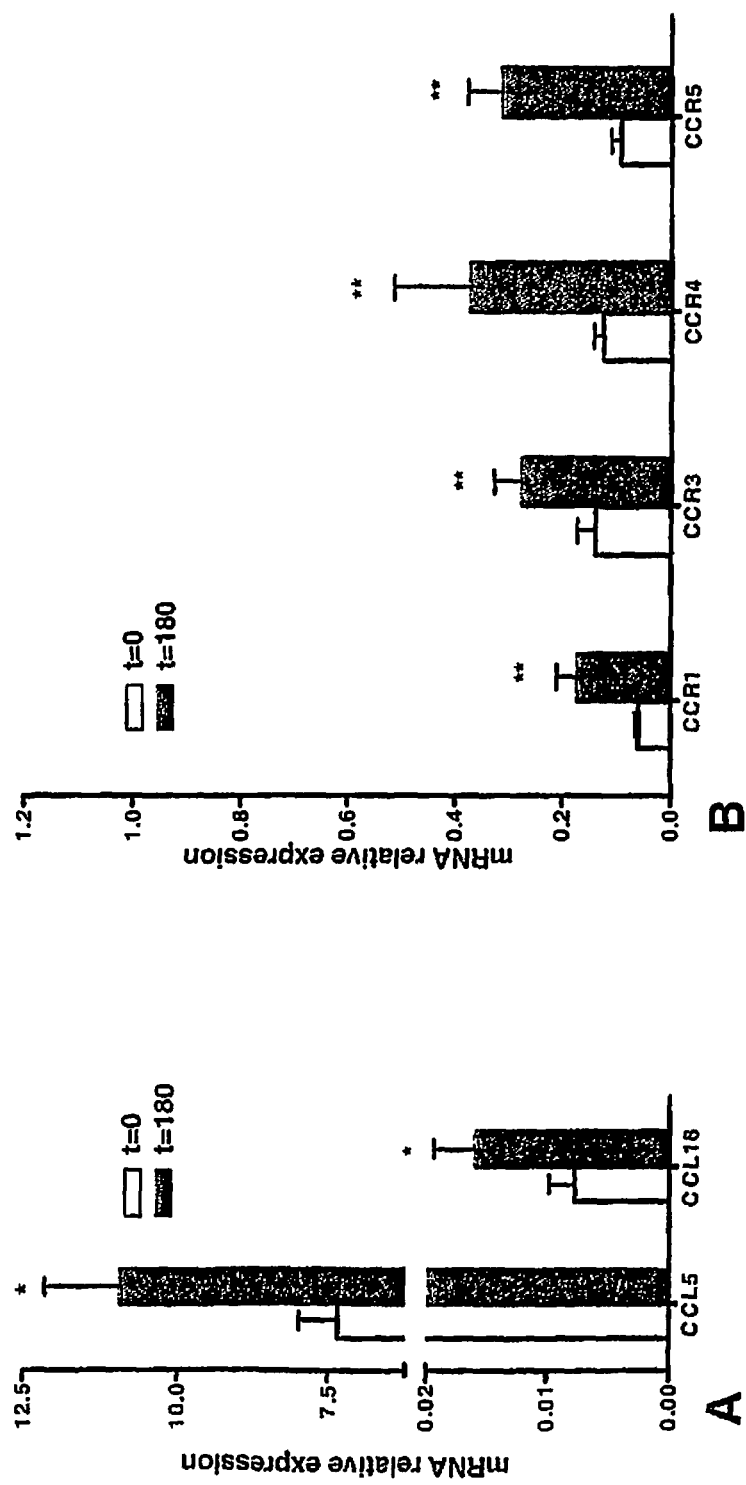
Figure 4:
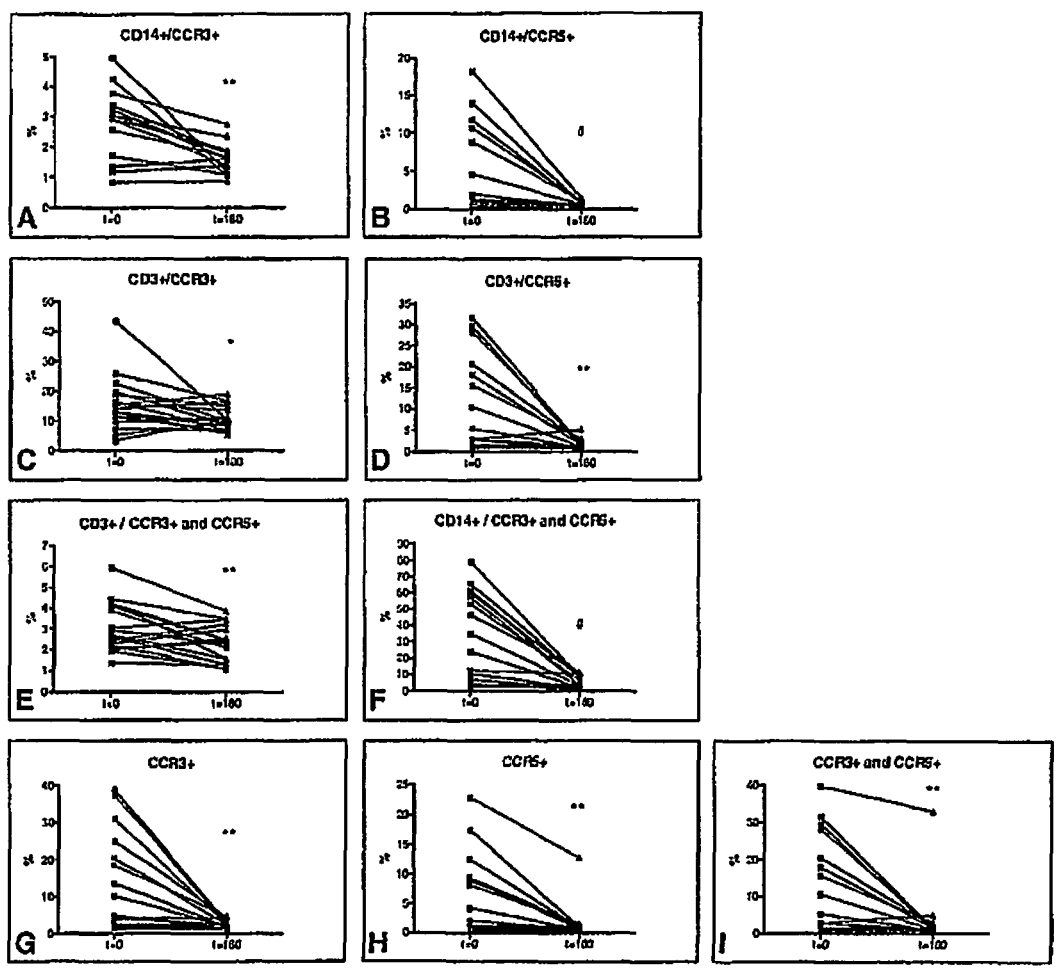

While the interaction of CCL5 with CCR1, CCR3, CCR4 and CCR5 is well described, the actual receptor for CCL18 is as yet unknown, which makes CCL18 currently an orphan ligand[17]. However, CCL18 has been reported to be a competitive inhibitor of CCL11 (eotaxin) binding to CCR3[18]. Therefore, we examined mRNA expression of chemokine receptors CCR1, CCR3, CCR4 and CCR5 as well as that of CCL5 and CCL18 in PBMCs, We observed a remarkable highly significant down-regulation of all four involved chemokine receptors at baseline (t=0) compared to PBMCs at t=180 (FIG. 3B). A similar temporal pattern was seen for CCL5 and CCL18, with CCL5 being abundantly expressed in PBMCs and CCL18 at only minor levels (FIG. 3A). Subsequent FACS analysis to detect CCR3 and CCR5 expression on CD3+ T-cells and CD14+ monocytes to our surprise revealed a significant elevated protein expression of CCR3 and CCR5 in both CD3+ and CD 14+ cells at t=0 compared with t=180 (FIG. 4A-D) (see comment p.28). Triple staining for CD3 or CD14 with CCR3 and CCR5 showed an increased chemokine receptor expression in the CD3+ population (3.1% triple positive cells at t=0 vs. 2.3% at t=180; P=0.007) and even more prominently so in the CD14+ cells (32.1% vs. 5.1% at t=0 and t=180, respectively; P<0.001). An identical pattern was seen for the percentage of CCR3+ and CCR5+ cells as well as of the combined CCR3+/CCR5+ cells in the total PBMC population (FIG. 4G-I).

Figure 8:
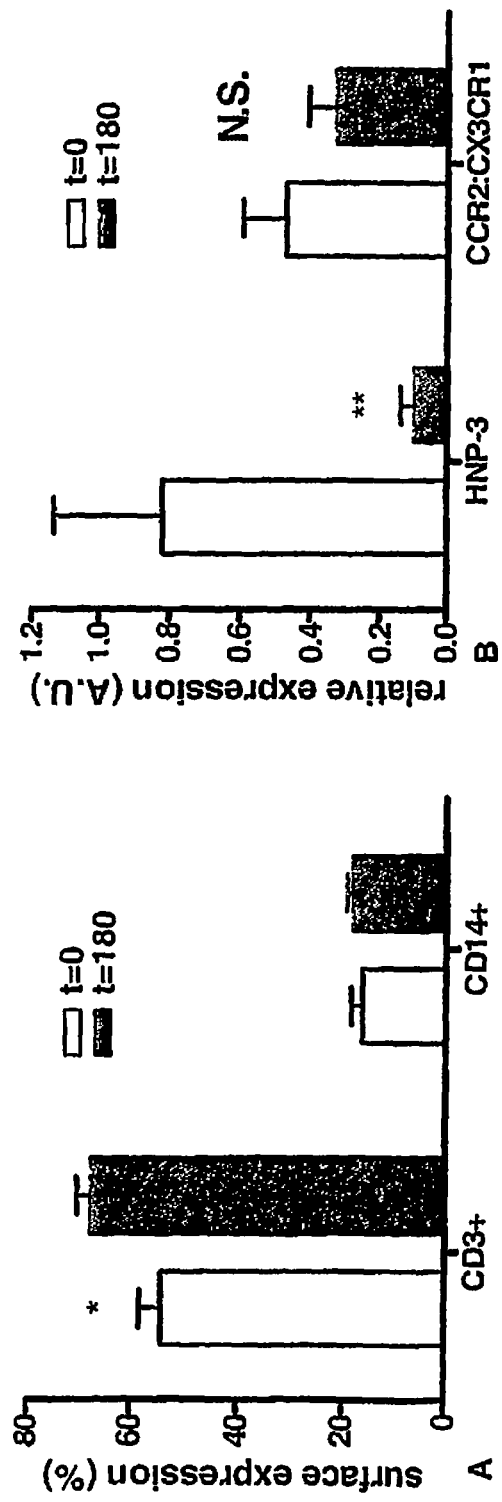

To assess whether the reduced gene expression pattern at baseline were caused by transient shifts in the leukocyte distribution profile we have monitored the total percentage of CD14+ (monocytes) and CD3+ cells (T-lymphocytes) in the PBMCs. Monocyte counts were not different between the two time points, whereas CD3+ cells were slightly decreased at t=0 (54.2 vs. 66.6%; P=0.01)(FIG. 8A) see p.28. A further study revealed no differences in the expression ratio of CCR2: CX3CR1, a measure of monocyte subset distribution[19], in PBMCs as well. We did however observe significantly elevated expression levels of HNP-3, a selective neutrophil marker, at t=0, pointing to an enhanced release of neutrophils during UAP (FIG. 8B) see p.28. Conceivably, the observed changes in chemokine receptor expression at t=0 may at least partly be attributed to the increased neutrophil counts. In contrast to chemokine plasma levels, no differences in expression level were seen for chemokine receptors between stabilised and refractory patients at t=0 (data not shown).

PBMC Stimulation Assay

In part however, the chemokine receptor down-regulation may reflect a feedback response on the immunomodulator burst after UAP. To verify if the observed expressional regulation of CCR1, CCR3, CCR4 and CCR5 in PBMCs is related to the elevated CCL5 and CCL18 levels during ischemic events, we stimulated PBMCs with rCCL5 and/or sCCL18. After 6 hours of stimulation, we observed no differential effect on CCR1, CCR4 and CCR5 mRNA expression. In sharp contrast however, sCCL18 caused a dramatic down-regulation in CCR3 expression, and this effect was further amplified by co-incubation with rCCL5 (P<0.01, FIG. 5A-D). Therefore, the down-regulation of CCR3 mRNA in PBMCs observed in vivo could be caused by the increased levels of CCL18. The down-regulation of CCR1, CCR4 and CCR5 in vivo might well be regulated by ligands other than CCL5 and CCL18.

Discussion

To our knowledge, this is the first study to describe the profiling of an extensive panel of chemokines by multiplex assay in plasma of UAP patients in a prospective manner. Of all chemokines tested, only CCL5 and CCL18 levels were, independent of other inflammatory markers and sCD40L, seen to be transiently elevated in refractory versus stabilised patients at baseline and to decline within 6 months after onset of the UAP symptoms. These phenomena were accompanied by a sharp, probably CCL18 induced, decrease in mRNA expression of the cognate chemokine receptors CCR3 and CCR5 in PBMCs at day 0 versus day 180. Concomitantly CCR3 and CCR5 surface expression was found to be increased at baseline, possibly reflecting a rapid receptor exposure by PBMCs during ischemic symptoms. Both CCL5 and CCL18 also show predictive features regarding clinical outcome.

The multiplex panel contained various chemokines, which have previously been linked with atherosclerosis or cardiovascular disease, such as CCL2, CCL5, CCL11, CXCL8 and CXCL10[5]. CCL5 and CCL18 were the only two chemokines that were differentially regulated at baseline between refractory and stabilised patients. Refractory patients had severe sustained ischemic complaints despite anti-anginal medication warranting coronary angiography with or without percutaneous coronary intervention. Therefore, while the levels of other chemokines that have been implicated in CVD were relatively unaltered and while refractory patients do not generally differ from stabilised in the extent of general systemic inflammation, CCL5 and CCL18 might be exclusive chemokine markers of ischemia severity in patients with UAP.

CCL5 and CCL18 were selected for further temporal analysis for a 180 days follow up. As previously mentioned, the role of CCL5 as an inflammatory mediator in cardiovascular disease is widely recognized, and CCL5 levels were indeed seen to be raised in patients with acute coronary syndromes[9,20]. However, these studies examined CCL5 levels at hospitalisation and, with one single exception, did not include a prospective study design. Only Nomura et al. showed a drop in CCL5 levels 30 days in UAP patients after PCI, to levels comparable with the 180 day levels in our study[9]. Our data extend this observation, as they demonstrate that the decline in CCL5 levels is not a consequence of PCI, but an intrinsic feature of stabilised UAP patients. Although data on CCL5 reference levels are still lacking, CCL5 at 2 and 180 days post inclusion was very comparable to values reported in healthy controls by Parissis et al., suggesting that CCL5 levels had returned to baseline within 2 days after onset of the ischemic symptoms[21].

To gain further insight on the contribution of activated platelets to the CCL5 peak levels, we performed a temporal assessment of sCD40L[22]. We observed significantly elevated levels of sCD40L at baseline, which is in concordance with earlier studies and reflective of the enhanced platelet activation status in UAP[23,24]. However, the observed progressive decline in sCD40L levels at t=2 and t=180 after UAP has never been documented in patients with UAP and may illustrate the rapid restoration of sCD40L homeostasis after UAP. Furthermore, t=0 and t=2 levels correlated with CCL5 levels, suggesting that activated platelets may, directly or indirectly, be a major source of CCL5. Apart from its massive secretion by activated platelets, elevated CCL5 levels during UAP could also arise from activated T-lymphocytes and as a result of altered homeostasis in the ischemic tissue distal to the occlusion[25,26]. Since Rothenbacher et al. observed reduced CCL5 levels in patients with stable coronary heart disease compared to controls, acute inflammation per se can unlikely be held responsible for the transient increase in CCL5 during UAP[27]. This is underscored by our findings, as we observed a down-regulation of CCL5 mRNA expression in PBMCs at baseline compared to 180 days after onset of the ischemia. Whether the increased response in refractory patients reflects a more extensive platelet (or T-cell) activation or a higher capacity of platelets and T-cells to elaborate CCL5 remains to be determined.

Interestingly, CCL18 has not yet been associated with cardiovascular disorders in patient cohorts. CCL18 is present at high levels in blood and it is produced by antigen presenting cells and by eosinophils. It is thought to act in the primary immune response functioning as an attractant for T-cells, B lymphocytes and monocytes[17]. As previously mentioned however, its receptor has not been identified, albeit that CCL18 was reported to function as a neutral CCR3 antagonist[18]. Evidence on a direct role of CCL18 in cardiovascular disease is not conclusive and is limited to two descriptive studies documenting CCL18 expression in atherosclerotic plaques and in particular at sites of reduced stability[28,29] We now show that CCL18 plasma levels are increased in UAP patients and even more so in patients with refractory symptoms. CCL18 elevation is sustained transient but levels are lowered after 180 days. The actual source of the persistent CCL18 increase after UAP is less clear. CCL18 expression was down-regulated in PBMCs at baseline, disqualifying abundant production by these cells as major source of plasma CCL18. Conceivably, plasma levels may reflect a release from CCL18 containing vulnerable plaques[28]. CCL18 levels were negatively correlated with sCD40L levels, possibly pointing to a negative feedback response upon platelet activation. Further research will have to clarify its role in acute coronary syndromes.

It has been suggested that several chemokines can act in the pathogenesis of non-infarcted ischemic cardiomyopathy, as the prevailing reactive oxygen generation and hypoxia in the ischemic tissue will induce a chemokine response[30]. Illustratively, MCP-1 was seen to be up-regulated in the myocardium at least 7 days after ischemia in mice and associated with interstitial fibrosis and left ventricular dysfunction in absence of myocardial infarction[6]. CCL18 levels persisted at a high level for at least two days as well, and given its capacity to activate fibroblasts and increase collagen production, it is tempting to propose a similar role of CCL18 in injury healing[31]. It may not only modulate the attraction of leukocyte subsets but, as shown by Wimmer et al., CCL18 may also play a facilatory role in bone-marrow haematopoietic stem cell function[32]. Therefore, elevated CCL18 levels could contribute in the inflammatory response but also in progenitor cell mobilisation towards areas of myocardial ischemia in anticipation of the myocardial repair process.

Figure 5:
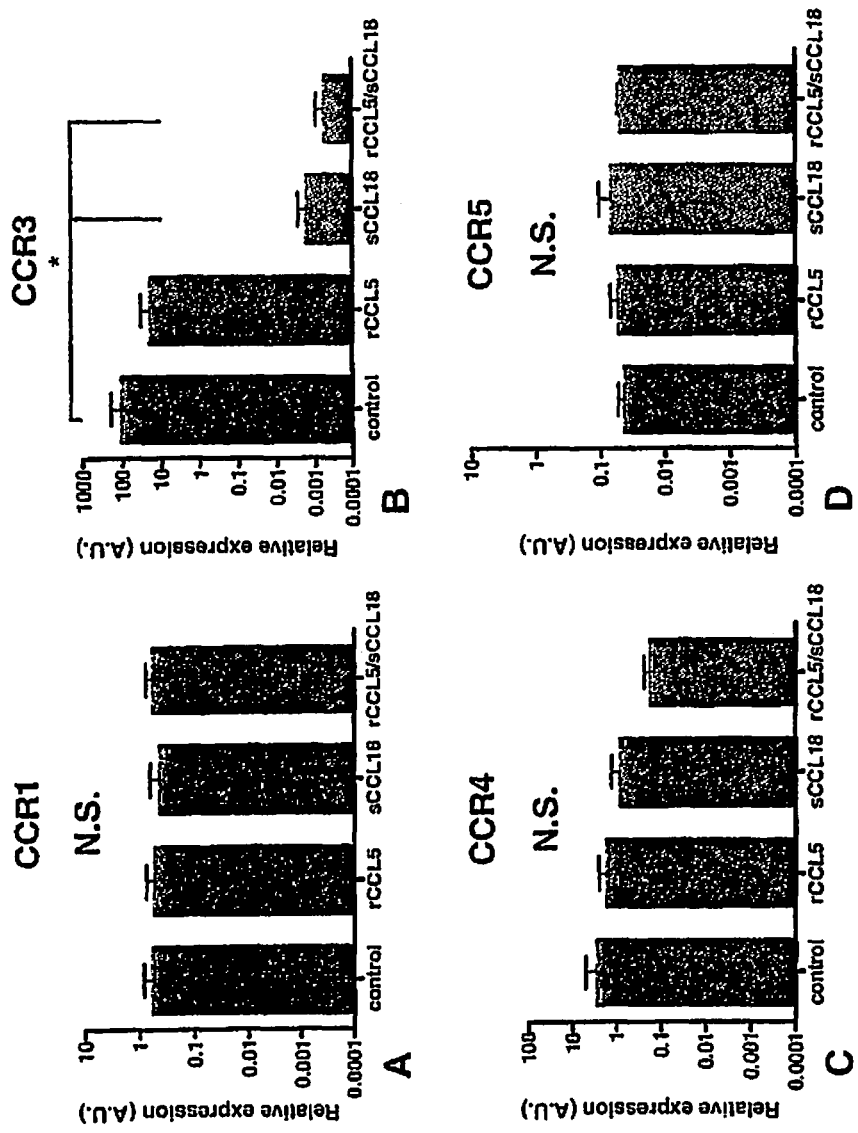

To further stress the role of CCL5 and CCL 18 in the pathophysiology of myocardial ischemia, we observed a significant increase in surface exposure of CCR3 and CCR5 by $CD3^+$ T-cells and $CD14^+$ monocytes and a paradoxical mRNA down-regulation of CCR1, CCR3, CCR4 and CCR5 at baseline. This is an intriguing and counter-intuitive observation, albeit that we are not the first to observe such a discrepancy between protein and mRNA chemokine receptor expression in PBMCs from UAP patients. In fact Damas et al. have reported a similar but opposite effect for CXCR4, i.e. down-regulation at the protein but up-regulation at the mRNA level in UAP compared with healthy control subjects, while levels of its ligand CXCL12 were lowered in patients with UAP compared to controls[33]. The rapid increase in surface protein exposure may result from acute mobilisation of intracellular receptors in response to enhanced plasma levels of the cognate ligands or of other actors that are released in unstable angina. The relative mRNA down-regulation of chemokine receptors in PBMCs may partly reflect a shifted leukocyte profile in UAP with a rapid mobilisation of HNP-3+ neutrophils as judged from the enhanced HNP-3 expression in PBMC mRNA at t=0[34], and a minor decrease in CD3+ cells, while total CD14+ levels remained unaffected. Partly however it may also be attributable to a negative feedback response to normalize exposed receptor levels as appears from our in vitro CCL18 regulation studies (FIG. 5). The transcriptional feedback may be effected in direct response to exposure of the surface receptors to CCL18, as CCR3 mRNA levels were dramatically decreased after exposure to sCCL18, thus identifying a new modulatory role of CCL18 in cardiac ischemia.

Examination of CCL5 and CCL18 quartile distribution shows a clear-cut relation with the occurrence of refractory symptoms. Furthermore, upper quartile levels also correlated with future cardiovascular events and revascularisation procedures, whereas sCD40L and CRP, which have been shown to have strong prognostic power in other studies[35-37], did not at this cohort size. Given the major cellular sources of CCL5 and CCL18, activated platelets and ischemic tissue, the increased levels in refractory UAP may reflect a more pronounced thrombosis and ischemia related induction in these patients. Whether or not it is causal in the refractory disease progression still remains to be clarified. Regarding the prognostic capacities of CCL5 and CCL18, the sensitivity and specificity of the upper quartile levels of the chemokines separately did not exceed 80%. Combining the upper two quartiles of both chemokines yielded a viable specificity of 90.3%, which thereby quite effectively rules out refractory symptoms for low CCL5 and CCL18 levels. However, although CCL5 and CCL18 may have potential as independent prospective biomarkers for disease, the correlations we observed between these chemokines and clinical severity of the symptoms as well as various follow-up parameters, albeit very significant, are currently not strong enough on its own. Therefore, the determination of plasma CCL5 and CCL18 levels, in combination with other clinical diagnostic parameters, could add prognostic features to the evaluation of patients with UAP. This issue needs to be addressed in future larger scale studies.

A few issues and limitations of this study should be noted. First, our set up principally precluded studying control levels of these chemokines before UAP. Nevertheless we believe that, as prospective analysis were performed in the same patients, conclusions on the temporal profile of CCL5 and CCL18 are justified. As all patients are largely symptom free at 180 days post UAP, we may safely assume that the latter values will approach the pre UAP levels of CAD patients. Second, it has recently been shown that statins can influence chemokine serum levels as well as chemokine receptor expression on PBMCs[8,38]. As we were in the fortunate circumstance that cohort sampling had taken place when statin therapy just began to emerge, only 8.2% of the patients of our cohort was on statin therapy. Since our data were corrected for this minor statin use, we believe that our results are not biased by statin therapy. Finally, the multiplex panel also comprised chemokines which have previously been linked to atherosclerosis or myocardial ischemia, including CCL2, CCL3, CXCL8 and CXCL10[21,39,40]. In our study, refractory unstable angina patients did not show significant differences for these chemokines nor for the other immunomodulators that had been assayed. These cytokines have thus not been selected for further temporal analysis but we cannot a priori rule out that these cytokines may affect unstable angina pectoris and myocardial ischemia.

Figure 9:
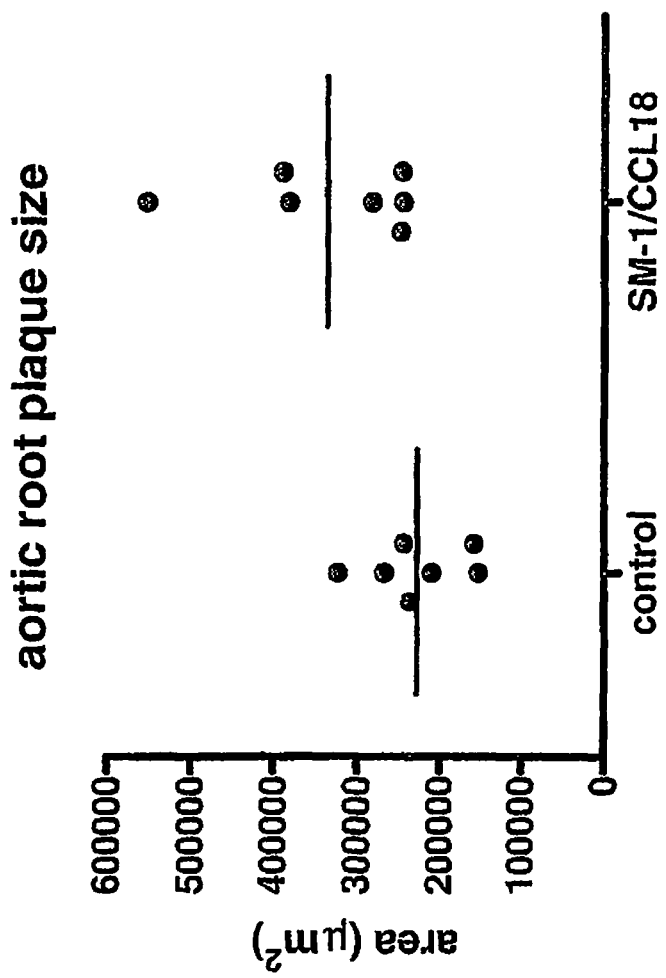

Furthermore, preliminary data in atherosclerosis prone ApoE−/− mice that already had developed collar induced carotid artery plaques showed that a 3 week intraperitoneal administration regimen of recombinant CCL18 aggravated lesion progression by a significant 50% (FIG. 9), suggesting that CCL18 may not only be a promising marker of cardiovascular disease but also a valid candidate for therapeutic intervention in cardiovascular disease.

To conclude, we identified CCL5 and particularly CCL18 as relevant chemokines in UAP. Whether they play a causative role in the pathogenesis or are more indirectly involved via other mechanisms, if these markers harbour any further diagnostic potential and if they are suitable therapeutic targets, needs to be addressed in future studies.

REFERENCES

1. Bertrand M E, Simoons M L, Fox K A, Wallentin L C, Hamm C W, McFadden E, De Feyter P J, Specchia G, Ruzyllo W. Management of acute coronary syndromes in patients presenting without persistent ST-segment elevation. *Eur Heart J.* 2002; 23:1809-40.
2. Hansson G K. Inflammation, Atherosclerosis, and Coronary Artery Disease. *N Engl J Med.* 2005; 352:1685-1695.
3. Charo I F, Taubman M B. Chemokines in the pathogenesis of vascular disease. *Circ Res.* 2004; 95:858-66.
4. Weber C. Platelets and chemokines in atherosclerosis: partners in crime. *Circ Res.* 2005; 96:612-6.
5. Kraaijeveld A O, de Jager S C, van Berkel T J, Biessen E A, Jukema J W. Chemokines and Atherosclerotic Plaque Progression: Towards Therapeutic Targeting? *Curr Pharm Des.* 2007; 13:1039-1052.
6. Dewald O, Frangogiannis N G, Zoerlein M, Duerr G D, Klemm C, Knuefermann P, Taffet G, Michael L H, Crapo J D, Welz A, Entman M L. Development of murine ischemic cardiomyopathy is associated with a transient inflammatory reaction and depends on reactive oxygen species. *Proc Natl Acad Sci USA.* 2003; 100:2700-5.
7. Charo I F, Ransohoff R M. The many roles of chemokines and chemokine receptors in inflammation. *N Engl J Med.* 2006; 354:610-21.
8. Damas J K, Boullier A, Waehre T, Smith C, Sandberg W J, Green S, Aukrust P, Quehenberger O. Expression of fractalkine (CX3CL1) and its receptor, CX3CR1, is elevated in coronary artery disease and is reduced during statin therapy. *Arterioscler Thromb Vasc Biol.* 2005; 25:2567-72.
9. Nomura S, Uehata S, Saito S, Ostumi K, Ozeki Y, Kimura Y. Enzyme immunoassay detection of platelet-derived microparticles and RANTES in acute coronary syndrome. *Thromb Haemost.* 2003; 89:506-12.
10. McDermott D H, Yang Q, Kathiresan S, Cupples L A, Massaro J M, Keaney J F, Jr., Larson M G, Vasan R S, Hirschhorn J N, O'Donnell C J, Murphy P M, Benjamin E J. CCL2 polymorphisms are associated with serum monocyte chemoattractant protein-1 levels and myocardial infarction in the Framingham Heart Study. *Circulation.* 2005; 112:1113-20.
11. de Lemos J A, Morrow D A, Sabatine M S, Murphy S A, Gibson C M, Antman E M, McCabe C H, Cannon C P, Braunwald E. Association between plasma levels of monocyte chemoattractant protein-1 and long-term clinical outcomes in patients with acute coronary syndromes. *Circulation.* 2003; 107:690-5.
12. de Jager W, to Velthuis H, Prakken B J, Kuis W, Rijkers G T. Simultaneous detection of 15 human cytokines in a single sample of stimulated peripheral blood mononuclear cells. *Clin Diagn Lab Immunol.* 2003; 10:133-9.
13. Verheggen P W, de Maat M P, Cats V M, Haverkate F, Zwinderman A H, Kluft C, Bruschke A V. Inflammatory status as a main determinant of outcome in patients with unstable angina, independent of coagulation activation and endothelial cell function. *Eur Heart J.* 1999; 20:567-74.
14. de Jager W, Prakken B J, Bijlsma J W, Kuis W, Rijkers G T. Improved multiplex immunoassay performance in human plasma and synovial fluid following removal of interfering heterophilic antibodies. *J Immunol Methods.* 2005.
15. Cusack M R, Marber M S, Lambiase P D, Bucknall C A, Redwood S R. Systemic inflammation in unstable angina is the result of myocardial necrosis. *J Am Coll Cardiol.* 2002; 39:1917-23.
16. Kennon S, Price C P, Mills P G, Ranjadayalan K, Cooper J, Clarke H, Timmis A D. The effect of aspirin on C-reactive protein as a marker of risk in unstable angina. *J Am Coll Cardiol.* 2001; 37:1266-70.
17. Schutyser E, Richmond A, Van Damme J. Involvement of CC chemokine ligand 18 (CCL18) in normal and pathological processes. *J Leukoc Biol.* 2005; 78:14-26.
18. Nibbs R J, Salcedo T W, Campbell J D, Yao X T, Li Y, Nardelli B, Olsen H S, Morris T S, Proudfoot A E, Patel V P, Graham G J. C-C chemokine receptor 3 antagonism by the beta-chemokine macrophage inflammatory protein 4, a property strongly enhanced by an amino-terminal alanine-methionine swap. *J Immunol.* 2000; 164:1488-97.
19. Tacke F, Alvarez D, Kaplan T J, Jakubzick C, Spanbroek R, Llodra J, Garin A, Liu J, Mack M, van Rooijen N, Lira S A, Habenicht A J, Randolph G J. Monocyte subsets differentially employ CCR2, CCR5, and CX3CR1 to accumulate within atherosclerotic plaques. *J Clin Invest.* 2007; 117:185-94.
20. Steppich B A, Moog P, Matissek C, Wisniowski N, Kuhle J, Joghetaei N, Neumann F J, Schomig A, Ott I. Cytokine profiles and T cell function in acute coronary syndromes. *Atherosclerosis.* 2007; 190:443-51.
21. Parissis J T, Adamopoulos S, Venetsanou K F, Mentzikof D G, Karas S M, Kremastinos D T. Serum profiles of C-C chemokines in acute myocardial infarction: possible implication in postinfarction left ventricular remodeling. *J Interferon Cytokine Res.* 2002; 22:223-9.
22. Andre P, Nannizzi-Alaimo L, Prasad S K, Phillips D R. Platelet-derived CD40L: the switch-hitting player of cardiovascular disease. *Circulation.* 2002; 106:896-9.
23. Aukrust P, Muller F, Ueland T, Berget T, Aaser E, Brunsvig A, Solum N O, Forfang K, Froland S S, Gullestad L. Enhanced levels of soluble and membrane-bound CD40 ligand in patients with unstable angina. Possible reflection of T lymphocyte and platelet involvement in the pathogenesis of acute coronary syndromes. *Circulation.* 1999; 100: 614-20.
24. Garlichs C D, Eskafi S, Raaz D, Schmidt A, Ludwig J, Herrmann M, Klinghammer L, Daniel W G, Schmeisser A. Patients with acute coronary syndromes express enhanced CD40 ligand/CD154 on platelets. *Heart.* 2001; 86:649-55.
25. Nelson P J, Kim H T, Manning W C, Goralski T J, Krensky A M. Genomic organization and transcriptional regulation of the RANTES chemokine gene. *J Immunol.* 1993; 151: 2601-12.
26. Weber C, Schober A, Zernecke A. Chemokines: key regulators of mononuclear cell recruitment in atherosclerotic vascular disease. *Arterioscler Thromb Vasc Biol.* 2004; 24:1997-2008.
27. Rothenbacher D, Muller-Scholze S, Herder C, Koenig W, Kolb H. Differential expression of chemokines, risk of stable coronary heart disease, and correlation with established cardiovascular risk markers. *Arterioscler Thromb Vasc Biol.* 2006; 26:194-9.
28. Reape T J, Rayner K, Manning C D, Gee A N, Barnette M S, Burnand K G, Groot P H. Expression and cellular localization of the CC chemokines PARC and ELC in human atherosclerotic plaques. *Am J Pathol.* 1999; 154:365-74.
29. Papaspyridonos M, Smith A, Burnand K G, Taylor P, Padayachee S, Suckling K E, James C H, Greaves D R, Patel L. Novel candidate genes in unstable areas of human atherosclerotic plaques. *Arterioscler Thromb Vasc Biol.* 2006; 26:1837-44.
30. Frangogiannis N G, Entman M L. Chemokines in myocardial ischemia. *Trends Cardiovasc Med.* 2005; 15:163-9.
31. Atamas S P, Luzina I G, Choi J, Tsymbalyuk N, Carbonetti N H, Singh I S, Trojanowska M, Jimenez S A, White B. Pulmonary and activation-regulated chemokine stimulates collagen production in lung fibroblasts. *Am J Respir Cell Mol Biol.* 2003; 29:743-9.
32. Wimmer A, Khaldoyanidi S K, Judex M, Serobyan N, Discipio R G, Schraufstatter I U. CCL18/PARC stimulates hematopoiesis in long-term bone marrow cultures indirectly through its effect on monocytes. *Blood.* 2006; 108: 3722-9.
33. Damas J K, Waehre T, Yndestad A, Ueland T, Muller F, Eiken H G, Holm A M, Halvorsen B, Froland S S, Gullestad L, Aukrust P. Stromal cell-derived factor-1 alpha in unstable angina: potential antiinflammatory and matrix-stabilizing effects. *Circulation.* 2002; 106:36-42.
34. Hansen P R. Role of neutrophils in myocardial ischemia and reperfusion. *Circulation.* 1995; 91:1872-85.
35. Kinlay S, Schwartz G G, Olsson A G, Rifai N, Sasiela W J, Szarek M, Ganz P, Libby P. Effect of atorvastatin on risk of recurrent cardiovascular events after an acute coronary syndrome associated with high soluble CD40 ligand in the Myocardial Ischemia Reduction with Aggressive Cholesterol Lowering (MIRACL) Study. *Circulation.* 2004; 110: 386-91.
36. Varo N, de Lemos J A, Libby P, Morrow D A, Murphy S A, Nuzzo R, Gibson C M, Cannon C P, Braunwald E, Schonbeck U. Soluble CD40L: risk prediction after acute coronary syndromes. *Circulation.* 2003; 108:1049-52.
37. Lindahl B, Toss H, Siegbahn A, Venge P, Wallentin L. Markers of myocardial damage and inflammation in relation to long-term mortality in unstable coronary artery disease. FRISC Study Group. Fragmin during Instability in Coronary Artery Disease. *N Engl J Med.* 2000; 343:1139-47.
38. Veillard N R, Braunersreuther V, Arnaud C, Burger F, Pelli G, Steffens S, Mach F. Simvastatin modulates chemokine and chemokine receptor expression by geranylgeranyl isoprenoid pathway in human endothelial cells and macrophages. *Atherosclerosis.* 2006; 188:51-8.
39. Gerszten R E, Garcia-Zepeda E A, Lim Y C, Yoshida M, Ding H A, Gimbrone M A, Jr., Luster A D, Luscinskas F W, Rosenzweig A. MCP-1 and IL-8 trigger firm adhesion of monocytes to vascular endothelium under flow conditions. *Nature.* 1999; 398:718-23.
40. Heller E A, Liu E, Tager A M, Yuan Q, Lin A Y, Ahluwalia N, Jones K, Koehn S L, Lok V M, Aikawa E, Moore K J, Luster A D, Gerszten R E. Chemokine CXCL10 promotes atherogenesis by modulating the local balance of effector and regulatory T cells. *Circulation.* 2006; 113:2301-12.

EXAMPLE 2

CCL3 (MIP-1α) levels are elevated during acute coronary syndromes and show strong prognostic power for future ischemic events.

Methods
Patient Cohorts
Mission

Study populations were compiled from the MISSION! intervention study[12]. The AMI patient group consisted of 44 patients (54.5% male; mean age 61.8±11.6 years) diagnosed with AMI on the basis of ECG and clinical chemical parameters (elevated troponin and creatine kinase levels). The control group represented 22 non-symptomatic age and sex matched subjects (54.5% male; mean age 61.7±12.8), not suffering from manifest coronary artery disease (Table 5). Baseline blood samples of AMI patients were taken within 2 hours after hospitalization and within 6 hours upon onset of AMI. Patients suffering from autoimmune disease, malignancies, chronic inflammatory diseases as rheumatoid arthritis or receiving immunosuppressant or chemotherapy were excluded from the study. This study was approved by the local ethics committee and all patients and healthy volunteers gave informed consent before being recruited. The investigation conformed to the principles outlined in the Helsinki Declaration.

Aprais

Plasma samples of patients with unstable angina, derived from the well defined APRAIS (Acute Phase Reaction and Ischemic Syndromes) study, were used to determine circulating CCL3 levels[13]. In brief, 54 patients who were admitted to the emergency department of the Leiden University Medical Center between March and September 1995 with unstable angina pectoris Braunwald class IIIB were included and followed for up to 18 months. Venous blood samples were obtained on admission (t=0) after 2 (t=2) and 180 days after admission (t=180), centrifuged and plasma aliquots were stored at −80° C. until further analysis. All patients had received standard medical therapy, i.e. aspirin 300 mg orally, nitro-glycerine intravenously and heparin infusion based titrated to the activated partial thromboplastin time. All subjects gave written informed consent and the study protocol was approved by the Ethics Committee of the Leiden University Medical Center.

Multiplex Chemokine Assay

Circulating chemokines levels of CCL2, CCL3, CCL5, CCL11, CCL17, CCL18, CCL22, CXCL8, CXCL9, and CXCL10 as well as four reference cytokines were determined in the MISSION! cohort, as well as CCL3 levels in the APRAIS cohort, by using a highly sensitive fluorescent microsphere based readout as described earlier[14,15]. Briefly, plasma samples were filtered and subsequently diluted with 10% normal rat and mouse serum (Rockland, Gilvertsville, Pa.) to block residual non-specific antibody binding. 1000 microspheres were added per chemokine (10 μl/well) in a total volume of 60 μl, together with standard and blank samples, and the suspension incubated for 1 hour in a 96 well filter plate at room temperature (RT). Then, 10 μl of biotinylated antibody mix (16.5 μg/ml) was added and incubated for 1 hour at RT. After washing with PBS-1% BSA-0.5% Tween 20, beads were incubated with 50 ng/well streptavidin R-phycoerythrin (BD Biosciences, San Diego, Calif.) for 10 minutes. Finally, beads were washed again with PBS-1% BSA-0.5% Tween 20, and the fluorescence intensity was measured in a final volume of 100 μl high-performance ELISA buffer (Sanquin, Amsterdam, the Netherlands). Measurements and data analysis were performed with the Bio-Plex Suspension Array system in combination with the Bio-Plex Manager software version 3.0 (Bio-Rad laboratories, Hercules, Calif.).

Murine Myocardial Infarction

Mice were anaesthetized and artificially ventilated with a mixture of oxygen and $N_2O$ [1:2 (vol/vol)] using a rodent ventilator (Harvard Apparatus, Holliston, Mass.) to which 2-2.5% isoflurane (Abbott Laboratories, Hoofddorp, the Netherlands) was added for anesthesia. Myocardial infarction was induced by permanent ligation of the proximal left anterior descending coronary artery with a sterile 7/0 silk suture (Ethicon, Johnson & Johnson, Amersfoort, the Netherlands). Three hours after ligation the mice were sacrificed, PBMCs and spleens were isolated for flow cytometric analysis and plasma was harvested for chemokine detection. All animal procedures were approved by the Animal Ethics Committee of Leiden University.

Elisa And Other Assays

Human as well as murine CCL3 levels (Biosource, Carlsbad, Calif.), murine CXCL10 (R&D systems, Minneapolis, Minn.) and murine IL-6 (eBioscience, San Diego, Calif.) were determined by sandwich Elisa assays as described by the manufacturers protocol. Baseline inflammatory parameters in the APRAIS cohort, such as C-reactive protein, fibrinogen and erythrocyte sedimentation rate (ESR), were determined as described previously[13]. Soluble CD40 ligand (sCD40L) was determined via a highly sensitive immunoassay (Quantakine HS, R&D Systems, Minneapolis, Minn.).

Flow Cytometry

PBMCs were isolated from whole blood by ablation of the erythrocytes. Splenocytes were isolated by squeezing spleens through a 70 μm cell strainer (BD falcon, BD Biosciences, San Jose, Calif.). After collection total blood cells and splenocytes were incubated with erythrocytes lysis buffer for 5 minutes on ice. Cells were centrifuged for 5 minutes and resuspended in lysis buffer. Residual erythrocytes were lysed by 5 minute incubation on ice. Cells were washed twice with PBS and counted. Consequently cells were stained for CD4, CCR3, CCR5 (BD Biosciences), CD8, F4/80 (eBioscience) and CXCR3 (US biological, Swampscott, Mass.) surface markers by adding 0.25 μg antibody per sample. After 45 minutes incubation on ice, cells were washed with PBS and subsequently analyzed by flow cytometry (FACScalibur, BD biosciences).

Statistical Methods

Statistical analysis was performed using SPSS version 13.0 (SPSS, Chicago, Ill.) All values are expressed as mean E standard error of mean. Differences in risk factor distribution between the control and the AMI group were analyzed with a Fishers Exact probability test. Chemokine data were tested for normal distribution by use of a Kolmogorov-Smirnov analysis. Non-Gaussian distributed data were analyzed by a Mann-Whitney U test, whereas normally distributed variables were analyzed by Student's t-test. Correlation analysis with inflammatory parameters was performed by Spearman's rank correlation test. Covariate adjustment for risk factors was performed by a univariate linear regression test. Quartile distribution of CCL3 was assessed and used for Chi-Square testing to associate elevated levels of CCL3 with future cardiovascular events. A P-value <0.05 was considered significant.

Results

Mission Patient Statistics

Two sub-cohorts were compiled at a 2:1 ratio as a pilot study revealed that the standard deviation in cytokine levels in the AMI population was on average 1.5 fold higher than that of the control subjects. AMI and control sub-cohorts were matched for gender, age and risk factors known to be associated with inflammatory status (type 2 diabetes mellitus, hypertension and hyperlipidemia). The AMI cohort encompassed a higher fraction of smokers and ex-smokers than the control cohort (56.8% in AMI compared to 22.7% in controls; P=0.01; Table 5). Therefore, all chemokine values were adjusted for smoking by univariate analysis. All proteins were all well within detectable range of the used assay.

TABLE 5

MISSION! Patient Characteristics

| | Controls | Acute Myocardial Infarction | P-value |
|---|---|---|---|
| Age (years) | 61.7 ± 2.6 | 61.8 ± 1.8 | 0.96 |
| Male/Female | 12/10 | 24/20 | 1.00 |
| Diabetes Mellitus | 3 (13.6%) | 6 (13.6%) | 1.00 |
| Hypertension | 8 (36.3%) | 11 (25%) | 0.39 |
| Total Cholesterol | 5.6 ± 0.3 mmol/L | 6.0 ± 0.1 mmol/L | 0.14 |
| Smoking | 5 (22.7%) 4 (18.1%) ex-smokers | 25 (56.8%)*; 4 (9.1%) ex-smokers | 0.01 |

Reference Panel

As a control for the validity of the multiplex assay a panel of reference cytokines and cell adhesion markers was included in the analysis. In compliance with previous findings plasma levels of IL-2 (0.07±0.06 pg/ml in controls vs. 0.65±0.28 in AMI; P=0.003), TNF-α (1.05±0.32 pg/ml in controls vs. 2.4±0.72 in AMI; P=0.03), sICAM-1 (476.1±80.7 ng/ml in controls vs. 713.0±49.9 in AMI; P=0.04) and IL-6 (9.8±4.1 in controls compared to 23.7±8.0 pg/ml in AMI; P=0.04) were significantly elevated in AMI patients (Table 6). Other general inflammation markers as IL-1α, IFN-γ and sVCAM-1 remained unchanged (data not shown), thereby showing that the AMI patient cohort was not enriched in subjects with a general hyperinflammatory status.

TABLE 6

APRAIS CCL3 t = 0 quartile levels as determined by multiplex

| Quartiles | CCL3 (pg/ml) |
|---|---|
| 1 | <41 |
| 2 | >41 and <53 |
| 3 | >53 and <83 |
| 4 | >83 |

Chemokines

Figure 13:
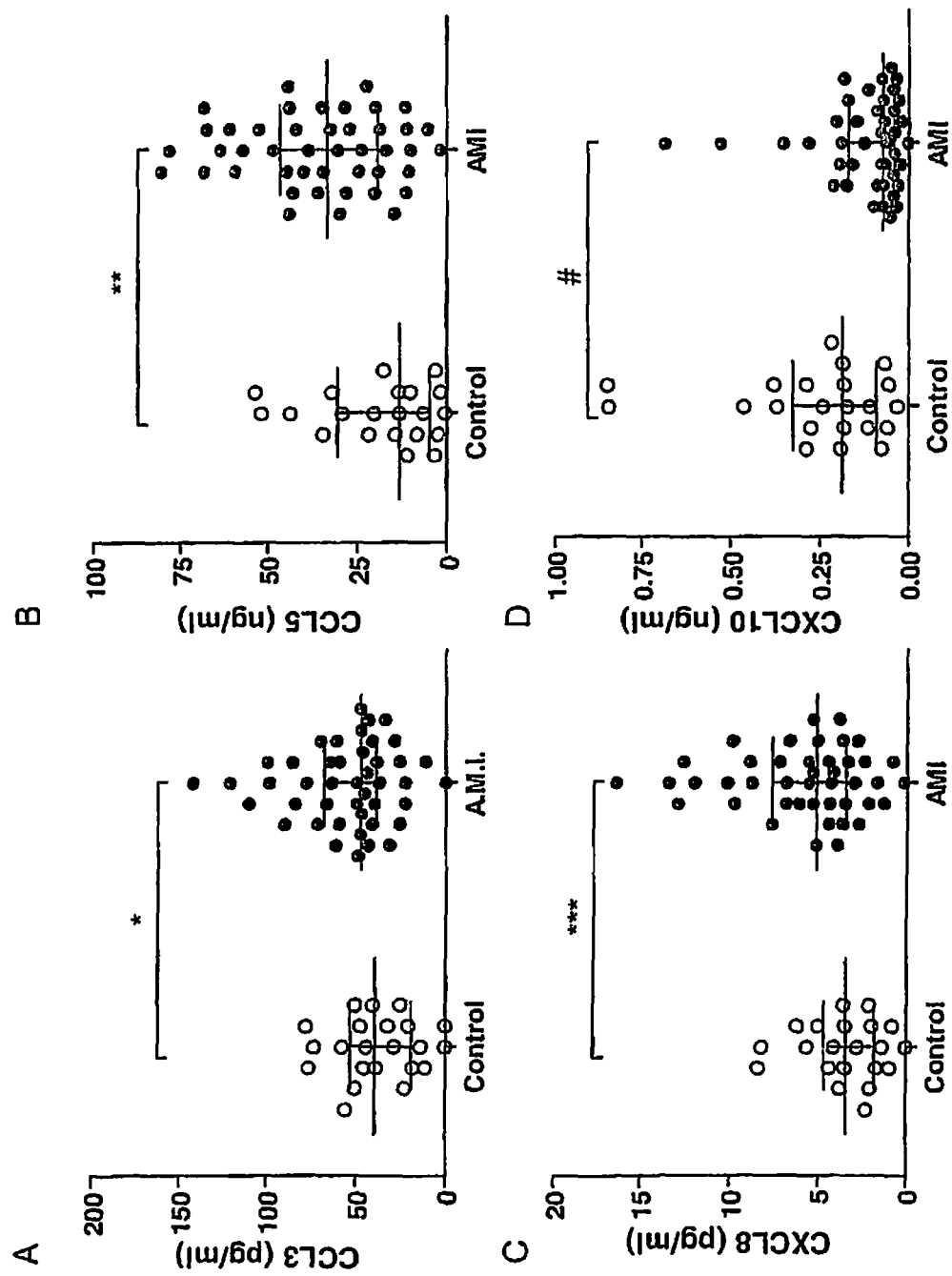
Figure 14:
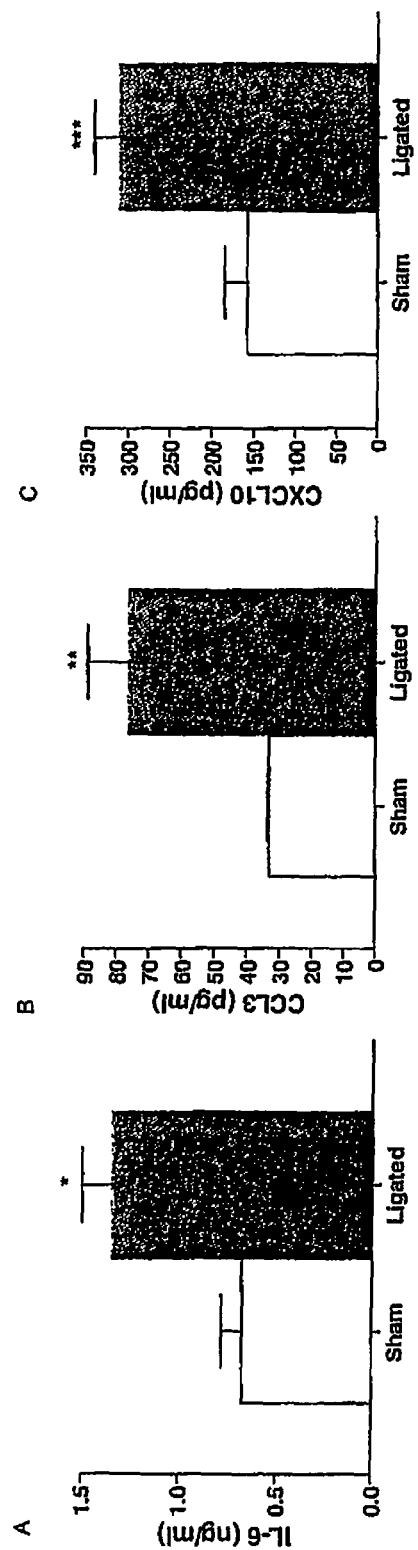

Plasma levels of the CC chemokines CCL3 (39.8 pg/ml, 21.3-50.3 IQR in controls compared to 47.8 pg/ml, 39.6-67.2 IQR in AMI; P=0.01: FIG. 13A) and CCL5 (13.4 ng/ml, 6.4-29.2 IQR in controls compared to 33.3 ng/ml, 19.1-45.3 in AMI; P=0.001: FIG. 14B) were significantly up-regulated in AMI compared to control patients (Table 7). After correction for cardiovascular risk factors CCL3 and CCL5 remained significantly elevated during AMI (P=0.025 and P=0.006 respectively). Of the CXC chemokines only CXCL8 (4.2±0.50 pg/ml in controls compared to 6.8±0.56 in AMI; P=0.01; FIG. 13C) was significantly up-regulated, while CXCL10 (255.1±47.2 pg/ml in control vs. 162.6±20.3 in AMI; P=0.002: FIG. 13D) was down-regulated in AMI compared to controls. After covariate adjustment both CXCL8 and CXCL10 remained significantly changed (P=0.02 and P=0.04 respectively). All other measured chemokines were not differentially regulated during AMI (Table 7).

TABLE 7

Mean Cytokine and Chemokine values

| | Control | AMI | | P | P* |
|---|---|---|---|---|---|
| IL-2 | 0.07 ± 0.06 pg/ml | 0.65 ± 0.28 pg/ml | ↑ | 0.003 | 0.047 |
| IL-6 | 9.8 ± 4.1 pg/ml | 23.8 ± 8.0 pg/ml | ↑ | 0.04 | 0.07 |
| TNFα | 0.6 pg/ml, (0-1.6) | 1.4 pg/ml, (0.5-2.4) | ↑ | 0.03 | 0.01 |
| sICAM-1 | 476 ± 80.7 ng/ml | 714 ± 50.0 ng/ml | ↑ | 0.045 | <0.001 |
| CCL2 | 305 ± 81 pg/ml | 522 ± 77 pg/ml | = | 0.08 | 0.14 |
| CCL3 | 49.8 pg/ml (21.3-50.6) | 47.7 pg/ml, (39.6-67.2) | ↑ | 0.02 | 0.025 |
| CCL5 | 13.4 ng/ml (6.4-29.2) | 33.3 ng/ml, (19.8-45.3) | ↑ | 0.001 | 0.006 |
| CCL11 | 15.9 pg/ml, (12.7-22.0) | 21.2 pg/ml, (13.6-29.8) | = | 0.27 | 0.33 |
| CCL17 | 16.4 pg/ml, (10.5-21.4) | 16.6 pg/ml, (8.6-28.9) | = | 0.46 | 0.26 |
| CCL18 | 555 ± 186 ng/ml | 681 ± 160 ng/ml | = | 0.18 | 0.85 |
| CCL22 | 356 pg/ml, (264-409) | 371 pg/ml, (296-549) | = | 0.11 | 0.08 |
| CXCL8 | 3.5 pg/ml, (1.9-4.3) | 5.1 pg/ml, (3.5-7.4) | ↑ | 0.004 | 0.02 |
| CXCL9 | 163 ± 51 pg/ml | 155 ± 25 pg/ml | = | 0.16 | 0.87 |
| CXCL10 | 255 ± 47.4 pg/ml | 120 ± 20.3 pg/ml | ↓ | 0.001 | 0.004 |

Reference (IL-2, IL-6, TNF-α and sICAM-1) and chemokine panel of measured parameters containing P value and corrected P value (P*) after adjustment for smoking. Values are expressed as mean±SEM or median with IQR when appropriate.

Aprais

Figure 11:
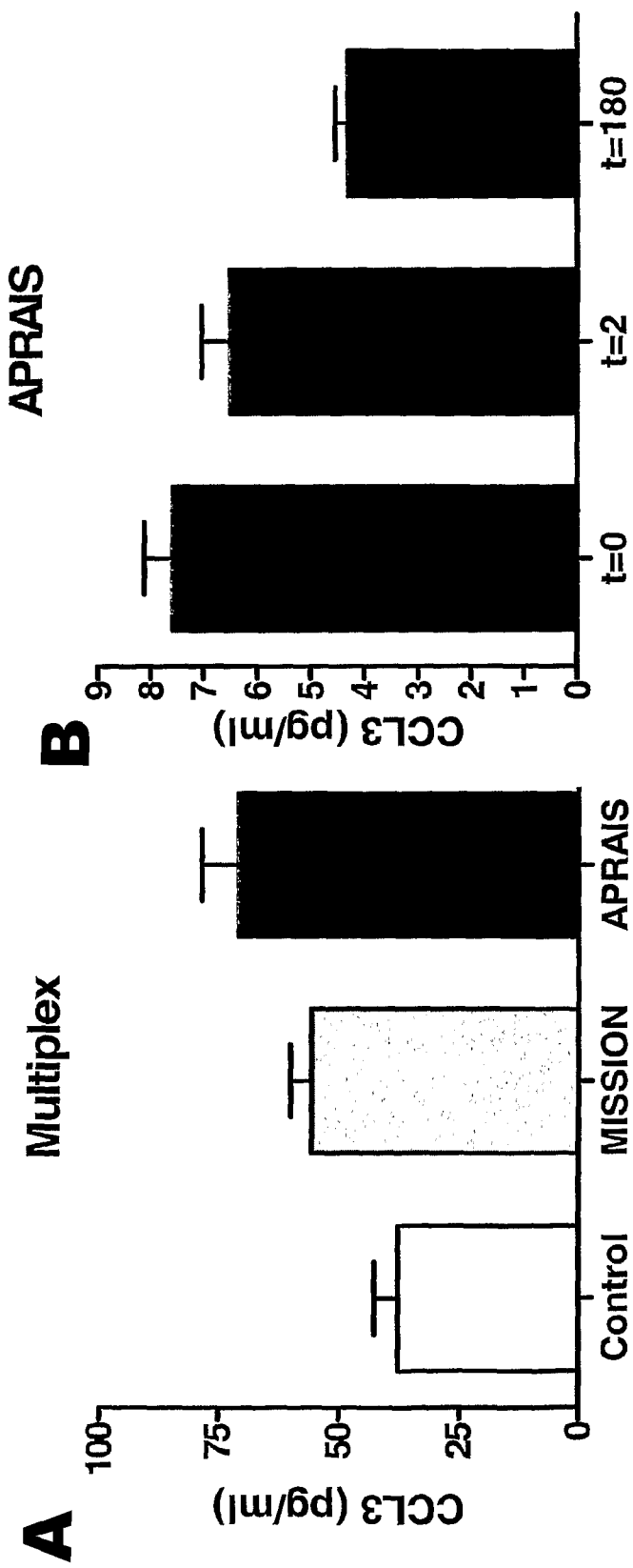
Figure 12:
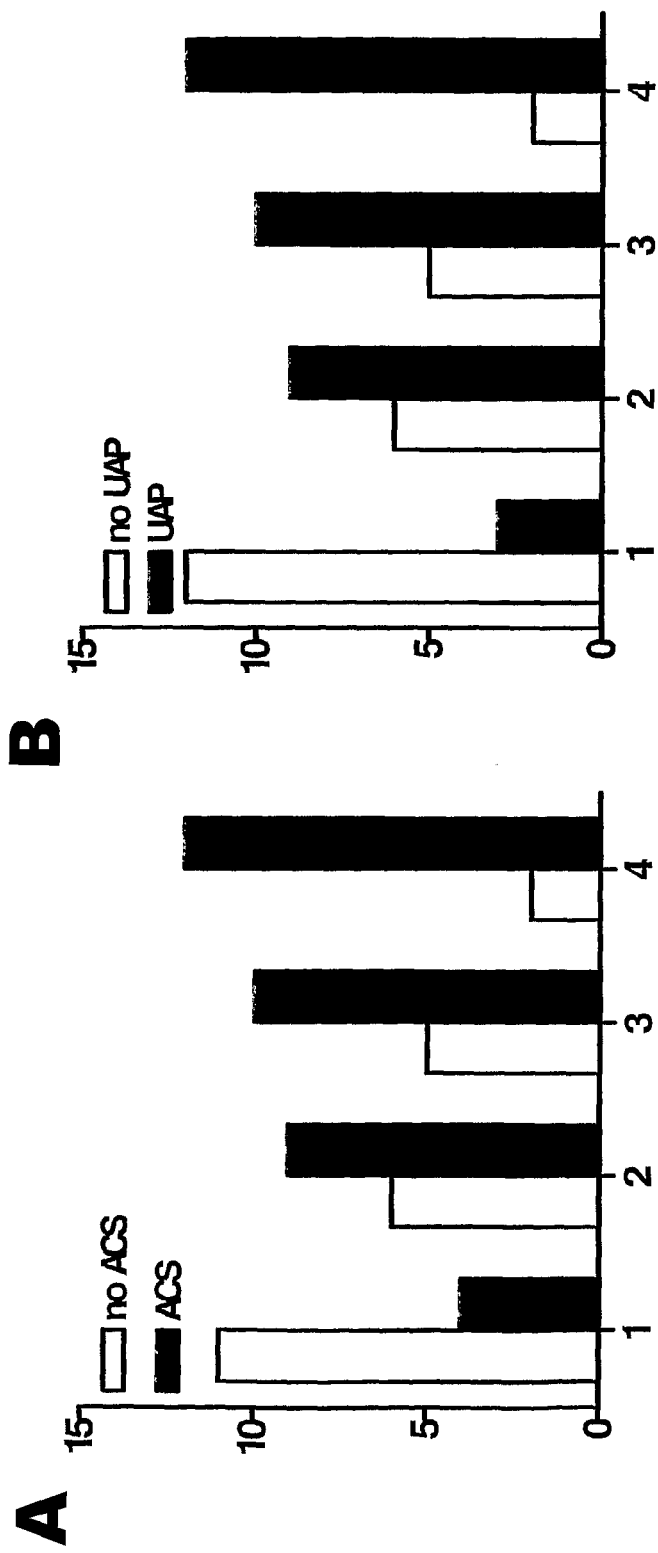

To verify this observation we compared CCL3 levels of the MISSION! cohort with those of the APRAIS cohort as described earlier refer to example 1. Inter-study analysis showed that patients with UAP also displayed similar increased CCL3 plasma levels compared to the MISSION! AMI patients (FIG. 11A). Next, we performed a temporal analysis of circulating CCL3 levels in the APRAIS cohort of patients with unstable angina pectoris. Plasma samples from baseline (t=0), t=2 and t=180, as analyzed by ELISA, revealed a significant decrease of CCL3 levels at t=180 compared with t=0 as well as t=2 (t=0 7.57 pg/ml; t=2 6.49 pg/ml; t=180 4.31 pg/ml, P<0.001) (FIG. 11B). Although absolute CCL3 plasma levels detected by ELISA were lower, comparison of both techniques revealed a highly significant correlation (R=0.92, P<0.001). Next, we sought to assess if CCL3 plasma levels had any potential to predict clinical outcome. Given the cohort size, multiplex CCL3 t=0 plasma levels were therefore categorized into quartiles and analyzed for correlation with the occurrence of ischemic symptoms during or immediately after hospitalisation and/or acute coronary syndromes (for quartile distribution, see Table 6). Upper quartile levels of CCL3 were highly predictive for the occurrence of acute coronary syndromes during follow-up (Likelihood ratio 11.52; P<0.01) and recurrent unstable angina pectoris during hospitalisation (Likelihood ratio 14.63; P<0.01) (FIG. 12A,B). Cardiac death during follow-up also showed a significant association, although less strong (Likelihood ratio 7.92; P<0.05)(data not shown). Finally, CCL3 did not correlate with any of the inflammatory parameters (data not shown). However, sCD40L levels revealed a significant negative correlation with CCL3 levels (R=−0.44; P=0.001), suggestive of a feedback response upon platelet activation.

Unlike CCL5 and CCL18, CCL3 levels was not predictive of a refractory nature of UAP (early stage) but highly significantly so of more mid term events occurring within 180 days after UAP.

Murine Myocardial Infarction

Figure 15:
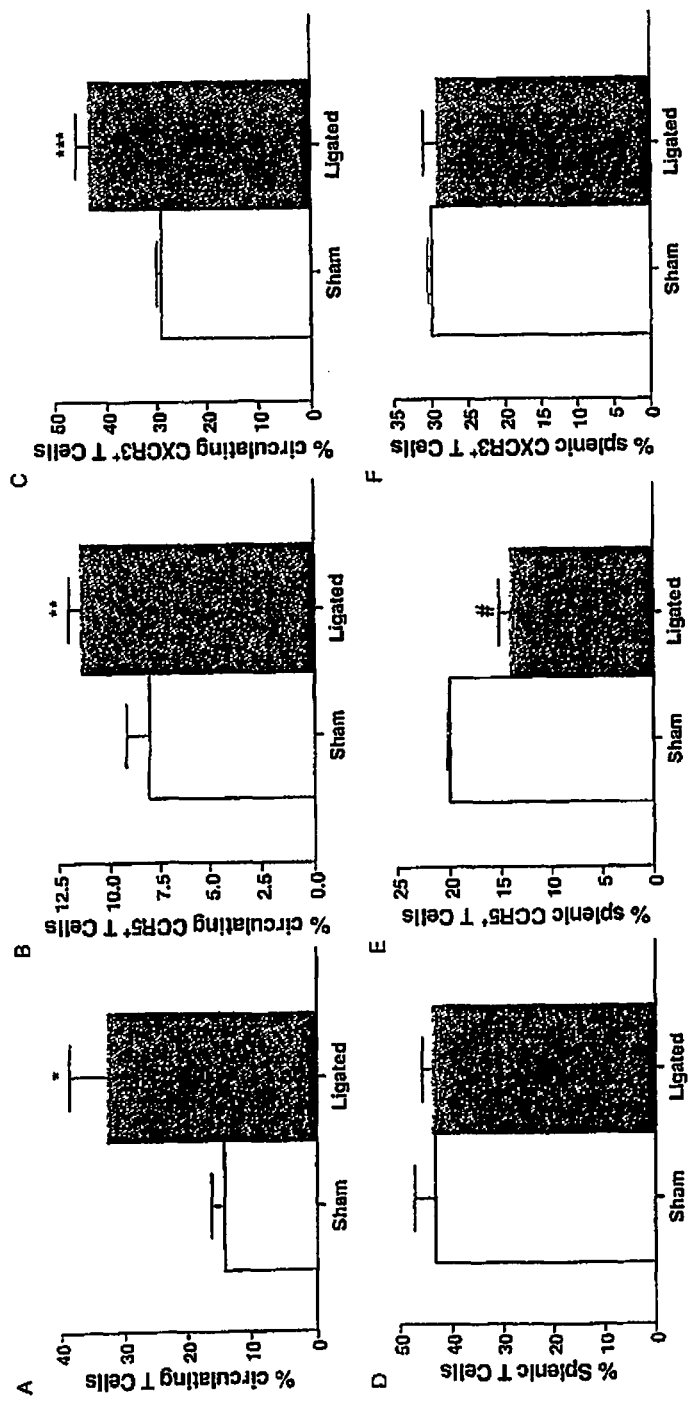

The obtained results in humans suggest an important role for CCL3 in ischemic myocardial injury. To ascertain whether the enhanced chemokines were ischemia related we performed myocardial infarction experiments in mice. Since the chemokines CCL5 and CXCL8 have been extensively studied regarding atherothrombosis and AMI we turned our interest to CCL3 and CXCL10. To induce acute myocardial infarction the left anterior descending coronary artery was ligated in C57Bl6 mice. CCL3 levels were, in concurrence with the earlier MISSION! findings, significantly elevated after AMI (33.2±1.5 vs. 76.4±37.4 pg/ml in ligated animals; P=0.02) (FIG. 14B). As a control for the AMI model, levels of the ischemia related cytokine IL-6 were measured[16,17]. IL-6 levels were significantly up-regulated after ligation (0.67±0.26 in sham vs. 1.34±0.46 ng/ml in ligated animals; P=0.007, FIG. 14A). Surprisingly the levels of CXCL10 were, opposed to the MISSION! findings, significantly enhanced after AMI (157.3±64.8 in sham operated compared to 310.6±86.6 pg/ml in ligated animals; P=0.03) (FIG. 14C). In addition PBMCs were harvested and analyzed for chemokine receptor expression on different cell subsets. As expected, the total T-cell population was enhanced in the circulation after ligation (14.1±3.8% in controls vs. 32.8±14.4% in ligated mice; P=0.038) while no effects were seen on splenic T-cells (P=0.9, FIGS. 15A and D respectively). Moreover the number of both circulating as well as splenic macrophages was not regulated by ischemic injury (data not shown). More extensive analysis of the T-cell population revealed a specific enrichment of $CCR5^+$ T-cells (8.0±2.0% in controls compared to 11.4±1.4% in ligated animals; P=0.02) (FIG. 15B). The enrichment in circulatory $CCR5^+$ T-cells was accompanied by a reduction in splenic $CCR5^+$ T-cells (19.95±0.5% vs. 14.1±3.1%; P=0.004) (FIG. 15E). CCR3 is the known receptor for the CCL3 related chemokine CCL4. As CCL3 and CCL4 are usually co-regulated we also analyzed PBMCs and splenocytes for CCR3 expression. The numbers of circulating $CCR3^+$ T-cells was very low. Analysis showed a slight, albeit not significant (P=0.24), increase in circulating $CCR3^+$ T-cells (data not shown). No differences in splenic $CCR3^+$ T-cells were evident (data not shown). Taken together these data suggest a CCL3 specific migration of T-cells from the secondary lymphoid organs towards the site of ischemic injury. In addition expression of the CXC chemokine receptor CXCR3 was determined on the circulating T-cells as well. In concurrence with the enhanced CXCL10 levels, the number of circulating $CXCR3^+$ T-cells was significantly increased after LAD ligation (29.1±1.9% vs. 43.5±5.7%; P=0.04) (FIG. 15C). However no effects on $CXCR3^+$ splenic T-cells were apparent (P=0.78) (FIG. 15F).

Figure 10:
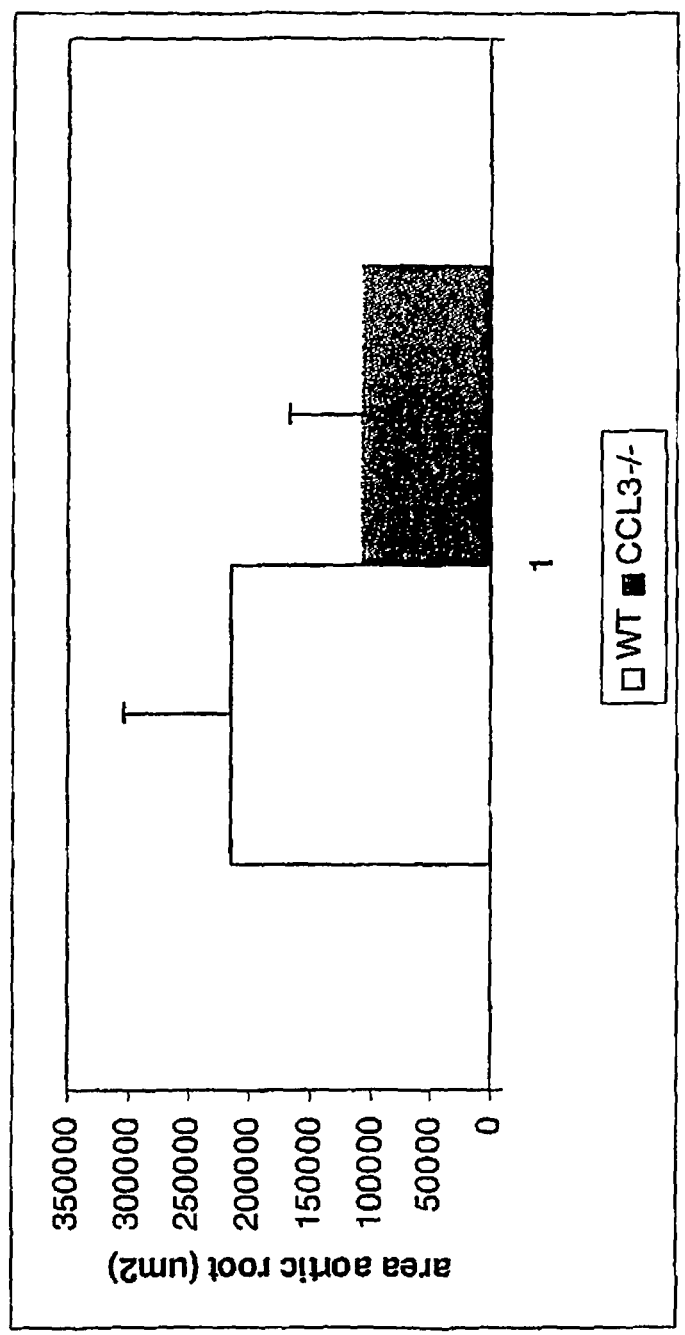

Preliminary data suggest that CCL3 levels not only are predictive of the risk of future cardiovascular events, but may also be causally implicated in disease development as atherosclerotic plaque growth in the aortic sinus of hyperlipidemic LDL receptor knockout mice with a leukocyte deficiency in CCL3 is significantly lower (−60%) than that in mice with normal leukocyte production of CCL3 (FIG. 10).

REFERENCES

1. Hansson G K. Inflammation, atherosclerosis, and coronary artery disease. *N Engl J Med*. 2005; 352:1685-95.
2. Laing K J, Secombes C J. Chemokines. *Dev Comp Immunol*. 2004; 28:443-60.
3. Weber C. Novel mechanistic concepts for the control of leukocyte transmigration: specialization of integrins, chemokines, and junctional molecules. *J Mol Med*. 2003; 81:4-19.
4. Weber C, Schober A, Zernecke A. Chemokines: key regulators of mononuclear cell recruitment in atherosclerotic vascular disease. *Arterioscler Thromb Vasc Biol*. 2004; 24:1997-2008.
5. Olson T S, Ley K. Chemokines and chemokine receptors in leukocyte trafficking. *Am J Physiol Regul Integr Comp Physiol*. 2002; 283 :R7-28.
6. Kraaijeveld A O, de Jager S C, van Berkel T J, Biessen E A, Jukema J W. Chemokines and atherosclerotic plaque progression: towards therapeutic targeting? *Curr Pharm Des*. 2007; 13:1039-52.
7. Mause S F, von Hundelshausen P, Zernecke A, Koenen R R, Weber C. Platelet Microparticles. A Transcellular Delivery System for RANTES-Promoting Monocyte Recruitment on Endothelium. *Arterioscler Thromb Vasc Biol*. 2005.
8. Simeoni E, Winkelmann B R, Hoffmann M M, Fleury S, Ruiz J, Kappenberger L, Marz W, Vassalli G. Association of RANTES G-403A gene polymorphism with increased risk of coronary arteriosclerosis. *Eur Heart J*. 2004; 25:1438-46.
9. Boger C A, Fischereder M, Deinzer M, Aslanidis C, Schmitz G, Stubanus M, Banas B, Kruger B, Riegger G A, Kramer B K. RANTES gene polymorphisms predict all-cause and cardiac mortality in type 2 diabetes mellitus hemodialysis patients. *Atherosclerosis*. 2005.
10. Frangogiannis N G. The role of the chemokines in myocardial ischemia and reperfusion. *Curr Vasc Pharmacol*. 2004; 2:163-74.
11. Tarzami S T, Miao W, Mani K, Lopez L, Factor S M, Berman J W, Kitsis R N. Opposing effects mediated by the chemokine receptor CXCR2 on myocardial ischemia-reperfusion injury: recruitment of potentially damaging neutrophils and direct myocardial protection. *Circulation*. 2003; 108:2387-92.
12. Liem S S, van der Hoeven B L, Oemrawsingh P V, Bax J J, van der Bom J G, Bosch J, Viergever E P, van Rees C, Padmos I, Sedney M I, van Exel H J, Verwey H F, Atsma D E, van der Velde E T, Jukema J W, van der Wall E E, Schalij M J. MISSION!: optimization of acute and chronic care for patients with acute myocardial infarction. *Am Heart J*. 2007; 153:14 e1-11.
13. Verheggen P W, de Maat M P, Cats V M, Haverkate F, Zwinderman A H, Kluft C, Bruschke A V. Inflammatory status as a main determinant of outcome in patients with unstable angina, independent of coagulation activation and endothelial cell function. *Eur Heart J*. 1999; 20:567-74.
14. de Jager W, to Velthuis H, Prakken B J, Kuis W, Rijkers G T. Simultaneous detection of 15 human cytokines in a single sample of stimulated peripheral blood mononuclear cells. *Clin Diagn Lab Immunol*. 2003; 10:133-9.
15. de Jager W, Prakken B J, Bijlsma J W, Kuis W, Rijkers G T. Improved multiplex immunoassay performance in human plasma and synovial fluid following removal of interfering heterophilic antibodies. *J Immunol Methods*. 2005; 300:124-35.
16. LaFramboise W A, Bombach K L, Dhir R J, Muha N, Cullen R F, Pogozelski A R, Turk D, George J D, Guthrie R D, Magovern J A. Molecular dynamics of the compensatory response to myocardial infarct. *J Mol Cell Cardiol*. 2005; 38:103-17.
17. Shu J, Ren N, Du J B, Zhang M, Cong H L, Huang T G. Increased levels of interleukin-6 and matrix metalloproteinase-9 are of cardiac origin in acute coronary syndrome. *Scand Cardiovasc J*. 2007; 41:149-54.
18. Miyao Y, Yasue H, Ogawa H, Misumi I, Masuda T, Sakamoto T, Morita E. Elevated plasma interleukin-6 levels in patients with acute myocardial infarction. *Am Heart J*. 1993; 126:1299-304.
19. Mizia-Stec K, Gasior Z, Zahorska-Markiewicz B, Janowska J, Szulc A, Jastrzebska-Maj E, Kobielusz-Gembala I. Serum tumour necrosis factor-alpha, interleukin-2 and interleukin-10 activation in stable angina and acute coronary syndromes. *Coron Artery Dis*. 2003; 14:431-8.
20. Wang Y N, Che S M, Ma A Q. Clinical significance of serum cytokines IL-1beta, sIL-2R, IL-6, TNF-alpha, and IFN-v in acute coronary syndrome. *Chin Med Sci J*. 2004; 19:120-4.
21. de Lemos J A, Hennekens C H, Ridker P M. Plasma concentration of soluble vascular cell adhesion molecule-1 and subsequent cardiovascular risk. *J Am Coll Cardiol*. 2000; 36:423-6.
22. Zhou R H, Shi Q, Gao H Q, Shen B J. Changes in serum interleukin-8 and interleukin-12 levels in patients with ischemic heart disease in a Chinese population. *J Atheroscler Thromb*. 2001; 8:30-2.
23. Hashmi S, Zeng Q T. Role of interleukin-17 and interleukin-17-induced cytokines interleukin-6 and interleukin-8 in unstable coronary artery disease. *Coron Artery Dis*. 2006; 17:699-706.

24. Parissis J T, Adamopoulos S, Venetsanou K F, Mentzikof D G, Karas S M, Kremastinos D T. Serum profiles of C-C chemokines in acute myocardial infarction: possible implication in postinfarction left ventricular remodeling. *J Interferon Cytokine Res.* 2002; 22:223-9.
25. Nomura S, Uehata S, Saito S, Osumi K, Ozeki Y, Kimura Y. Enzyme immunoassay detection of platelet-derived microparticles and RANTES in acute coronary syndrome. *Thromb Haemost.* 2003; 89:506-12.
26. Mause S F, von Hundelshausen P, Zernecke A, Koenen R R, Weber C. Platelet microparticles: a transcellular delivery system for RANTES promoting monocyte recruitment on endothelium. *Arterioscler Thromb Vasc Biol.* 2005; 25:1512-8.
27. Guan E, Wang J, Norcross M A. Identification of human macrophage inflammatory proteins 1alpha and 1beta as a native secreted heterodimer. *J Biol Chem.* 2001; 276:12404-9.
28. Vandervelde S, van Luyn M J, Rozenbaum M H, Petersen A H, Tio R A, Harmsen M C. Stem cell-related cardiac gene expression early after murine myocardial infarction. *Cardiovasc Res.* 2007; 73:783-93.
29. Hou Y, Plett P A, Ingram D A, Rajashekhar G, Orschell C M, Yoder M C, March K L, Clauss M. Endothelial-monocyte-activating polypeptide II induces migration of endothelial progenitor cells via the chemokine receptor CXCR3. *Exp Hematol.* 2006; 34:1125-32.
30. Waeckel L, Mallat Z, Potteaux S, Combadiere C, Clergue M, Duriez M, Bao L, Gerard C, Rollins B J, Tedgui A, Levy B I, Silvestre J S. Impairment in postischemic neovascularization in mice lacking the CXC chemokine receptor 3. *Circ Res.* 2005; 96:576-82.

Materials and Methods

Animals

LDLr$^{-/-}$ mice were obtained from the local animal breeding facility. Mice were maintained on sterilized regular chow (RM3; Special Diet Services, Essex, U.K.). Drinking water was supplied with antibiotics (83 mg/L ciprofloxacin and 67 mg/L polymyxin B sulfate) and 6.5 g/L sucrose and was provided ad libitum. Animal experiments were performed at the animal facilities of the Gorlaeus laboratories of the Leiden University. All experimental protocols were approved by the ethics committee for animal experiments of Leiden University.

Temporal Expression Profile

Male LDLr$^{-/-}$ mice were fed a Western type diet containing 0.25% cholesterol and 15% cacaobutter (Special Diet Services, Sussex, UK) two weeks prior to surgery and throughout the experiment. To determine gene expression levels in (n=20) mouse plaques, atherosclerotic carotid artery lesions were induced by perivascular collar placement as described previously[1]. Mice were anaesthetized by subcutaneous injection of ketamine (60 mg/kg, Eurovet Animal Health, Bladel, The Netherlands), fentanyl citrate and fluanisone (1.26 mg/kg and 2 mg/kg respectively, Janssen Animal Health, Sauderton, UK). From 0 to 8 weeks after collar placement every two weeks a subset of 4 mice was sacrificed. The animals were anaesthetized as described above and perfused through the left cardiac ventricle with PBS and exsanguinated by femoral artery transsection. Subsequently, both common carotid arteries were removed and snap-frozen in liquid nitrogen for optimal RNA preservation. The specimens were stored at −80° C. until further use.

RNA Isolation

Two or three carotids were pooled per sample and homogenized by grounding in liquid nitrogen with a pestle. Total RNA was extracted from the tissue using Trizol reagent according to manufacturer's instructions (Invitrogen, Breda, The Netherlands). RNA was reverse transcribed using M-MuLV reverse transcriptase (RevertAid, MBI Fermentas, Leon-Roth) and used for quantitative analysis of gene expression with an ABI PRISM 7700 Taqman apparatus (Applied Biosystems, Foster City, Calif.) as described previously[2], using murine hypoxanthine phosphoribosyltransferase (HPRT) and cyclophilin A (CypA) as standard housekeeping genes (Table 8).

Bone Marrow Transplantation

To induce bone marrow aplasia, male LDLr$^{-/-}$ recipient mice were exposed to a single dose of 9 Gy (0.19 Gy/min, 200 kV, 4 mA) total body irradiation using an Andrex Smart 225 Röntgen source (YXLON International) with a 6-mm aluminum filter 1 day before transplantation. Bone marrow was isolated from male CCL3$^{-/-}$ or littermates by flushing the femurs and tibias. Irradiated recipients received 0.5×10$^7$ bone marrow cells by tail vein injection and were allowed to recover for 6 weeks. Animals were placed on a western type diet containing 0.25% cholesterol and 15% cacao butter (SDS) diet for 12 weeks and subsequently sacrificed. Twenty four hours prior to sacrifice a subset of animals were injected intraperitoneally with lipopolysaccharide (LPS) (*Salmonella minnesota* R595 (Re) (List Biological Laboratories Inc., Campbell, Calif.)). Plasma levels of CCL3 were determined by sandwich Elisa(Biosource, Carlsbad, Calif., according to the manufacturer's protocol) to confirm impaired CCL3 production from leukocytes.

Histological Analysis

Cryostat sections of the aortic root (10 μm) were collected and stained with Oil-red-O. Lesion size was determined in 5 sections of the aortic valve leaflet area. Corresponding sections on separate slides were stained immunohistochemically with an antibody directed against a macrophage specific antigen (MOMA-2, monoclonal rat IgG2b, dilution 1:50; Serotec, Oxford, UK). Goat anti-rat IgG-AP (dilution 1:100; Sigma, St. Louis, Mo.) was used as secondary antibody and NBT-BCIP (Dako, Glostrup, Denmark) as enzyme substrates. Masson's trichrome staining (Sigma, St. Louis, Mo.) was used to visualize collagen (blue staining). Neutrophils were visualized by Naphtol AS-D Chloroacetate Esterase stain according to the manufacturer's protocol (Sigma).

Macrophage Stimulation

Serum deprived RAW264.7 macrophages were stimulated with 10 μg/ml ox-LDL or 1 ng/ml LPS for 24 hours. Total RNA was isolated for real time PCR to assess CCL3 expression. Serum deprived RAW 264.7 macrophages were stimulated with recombinant CCL3 (10 or 100 ng/ml) for 24 hours. Subsequently [$^3$H]-Thimidine (1 μCi/well, specific activity 24 Ci/mmol; Amersham Biosciences, The Netherlands) was added to each well and cells were allowed to proliferate for another 24 hours. Cells were rinsed twice with cold PBS and subsequently lysed with 0.1M NaOH. The amount of [$^3$H]-thymidine incorporation was measured using a liquid scintillation analyzer (Tri-Carb 2900R).

Cyclophosphamide Induced Neutropenia

Female CCL3$^{-/-}$ mice or WT control received an intraperitoneal (i.p) injection of cyclophosphamide (6 mg/mouse) to deplete blood neutrophils as described previously[3, 4]. Blood samples were taken via the tail vein regularly and blood cell differentiation was determined on a Sysmex cell differentiation apparatus (Goffin Meyvis, Etten-Leur, Nederland).

In Vivo Chemotaxis

Female CCL3−/− mice or WT control received an i.p. injection of 500 ng recombinant KC (Peprotech, Rocky Hill, N.J.) or PBS. Two hours later blood and peritoneal cells were isolated and analyzed for neutrophil composition by flow cytometry.

Flow Cytometry

Peritoneal leukocytes were harvested by peritoneal cavity lavage with PBS. Crude peripheral blood mononuclear cells (PBMC) and peritoneal leukocytes were incubated at 4° C. with erythrocyte lysis buffer (155 mM $NH_4CL$ in 10 mM Tris/HCL, pH 7.2) for 5 minutes. Cells were centrifuged for 5 minutes at 1500 rpm, resuspended in lysis buffer to remove residual erythrocytes. Cells were washed twice with PBS. Cell suspensions were incubated with 1% normal mouse serum in PBS and stained for the surface markers CD11b, GR1 and CD71 (eBioscience, San Diego, Calif.) at a concentration of 0.25 µg Ab/200,000 cells. Subsequently cells were subjected to flow cytrometric analysis (FACSCalibur, BD Biosciences, San Diego, Calif.). FACS data were analyzed with CELLQuest software (BD Biosciences).

Statistical Analysis

Data are expressed as mean±SEM. A 2-tailed Student's t-test was used to compare individual groups, while multiple groups were compared with a one-way ANOVA and a subsequent Student-Newman-Keuls multiple comparisons test. Non-parametric data were analyzed using a Mann-Whitney U test. A level of $P<0.05$ was considered significant.

Results

Figure 16:
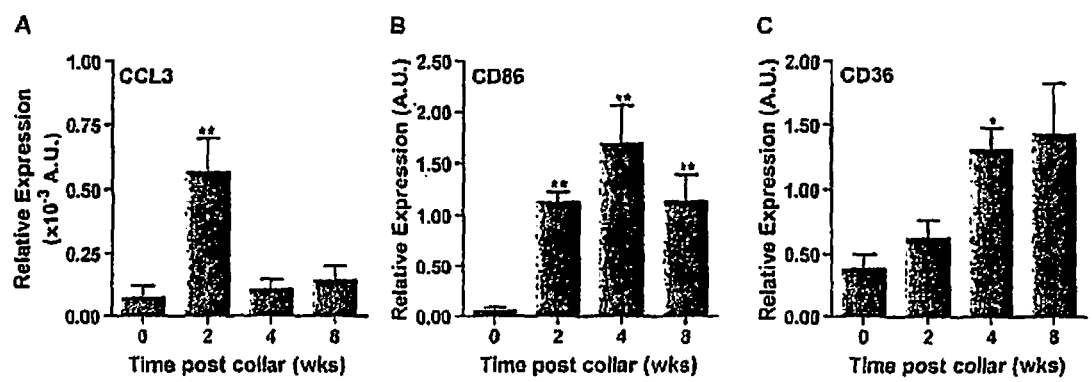
FIG. 16 shows temporal profiling of CCL3 expression in collar induced carotid artery plaques showed increased CCL3 production 2 weeks after collar placement (A). Rapid and steady induction was observed for the macrophage marker CD68 (B), while CD36 induction was somewhat delayed (C). **p<0.01 compared to base line (t=0).
Figure 17:
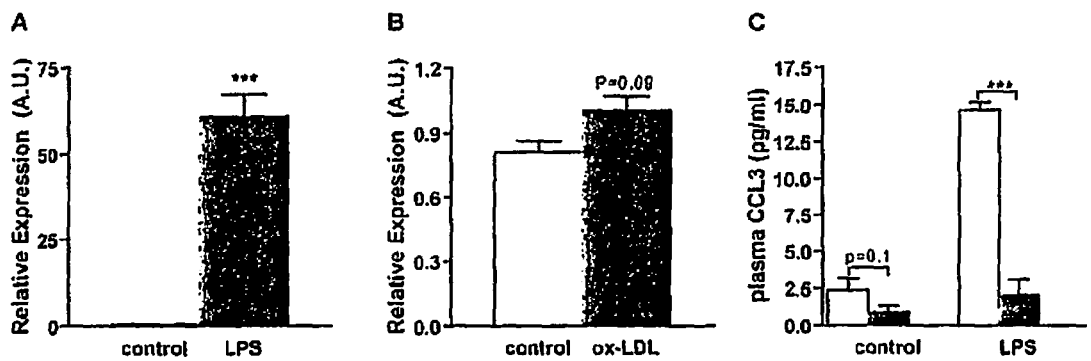
FIG. 17 shows CCL3 expression in macrophages is strongly upregulated upon LPS (50 ng/ml) (A) but not ox-LDL (10 ug/ml) (B) stimulation. LPS induced CCL3 response in vivo is ablated in CCL3−/− chimeras (C, black bars)) ***p<0.001.

Temporal expression analysis of atherosclerotic lesions in LDLr−/− mice showed a clearcut, transient upregulation of CCL3 in initial plaques (2 weeks after collar placement). At more advanced stages of lesion progression CCL3 is returning to its original level. This expression is initially accompanied by increased expression of macrophage marker CD68 of which its levels remain high at later time points. The expression of CD36 is somewhat delayed as compared to CD68 and CCL3 (FIG. 16). The expression profiles suggest that CCL3 may be involved in the critical recruitment of inflammatory cells to atherosclerotic lesion sites. In vitro exposure of RAW 264.7 macrophages to ox-LDL leads to a moderate induction of CCL3 expression, while the TLR4 ligand LPS strongly induces MIP1α at mRNA level (FIG. 17).

To assess effects of hematopoietic CCL3 deficiency on leukocyte migration and activation as well as on atherogenesis we reconstituted LDLr−/− mice with CCL3−/− bone marrow. CCL3 deficiency did not influence body weight or total cholesterol levels during the course of the experiment (data not shown). Plasma MIP1α levels were not significantly different between CCL3−/− chimeras and littermate controls (2.4±0.8 pg/ml in WT vs. 0.9±0.6 pg/ml in CCL3$^{-/-}$ chimeras; p=0.1, FIG. 17C). The CCL3 deficient phenotype was much more pronounced after in vivo treatment with LPS. Circulating MIP1α levels 24 h after LPS treatment were robustly increased in WT but not in CCL3−/− chimeras (14.7±0.4 pg/ml in control compared to 2.1±1.0 pg/ml in CCL3$^{-/-}$ chimeras; p=0.00005, FIG. 18A).

Lesion development in the aortic root of CCL3−/− chimeras was reduced by a significant 31% (135.1±76.5×10³ µm² in CCL3$^{-/-}$ compared to 198.4±51.4×10³ µm² in controls; P=0.04, FIG. 19A). The percentage of intimal MoMa-2+ macrophages was not different between groups (19.3±2.6% in controls vs. 22.9±3.0% in CCL3$^{-/-}$, FIG. 18B), suggesting that CCL3 alone may not be very critical in macrophage accumulation and proliferation in the atherosclerotic plaque. CD3 T cell numbers were not influenced by CCL3 deficiency (2.9±1.2 T cells/mm² plaque in controls and 2.6±1.5 T cells/mm² plaque in CCL3−/−, FIG. 18D). In contrast, the amount of plaque neutrophils (7.0±0.7 in WT compared to 2.9±0.8/mm² intimal tissue in CCL3$^{-/-}$ plaques; p=0.001, FIG. 18E), as well as neutrophil adherence were significantly reduced in CCL3$^{-/-}$ plaques (FIG. 18F). As measure of lesion progression stage intimal collagen deposition was determined. The percentage of collagen in CCL3$^{-/-}$ plaques was not influenced by CCL3 deficiency (7.5±1.4 in WT compared to 5.7±1.0% in CCL3$^{-/-}$ chimeras, FIG. 18C).

CCL3 deficiency did not influence the total number of circulating white blood cells in WT and CCL3$^{-/-}$ transplanted animals (4.4±0.7 in WT vs. 3.9±0.6×10⁶ cells/ml in CCL3$^{-/-}$, FIG. 19A) and the number of circulating monocytes was not affected by CCL3 deficiency as well (7.7±1.1 in WT vs. 8.9±1.0% in CCL3$^{-/-}$ chimeras, FIG. 19B). Interestingly the percentage of circulating neutrophils was significantly decreased in CCL3$^{-/-}$ chimeras (35.3±3.9 in WT vs. 23.6±2.5% in CCL3$^{-/-}$ chimeras; p=0.02, FIG. 19C).

The decreased neutrophil numbers may result from a reduced half life or an impaired differentiation and stromal egress of neutrophils. To investigate this, animals were treated with a single injection of cyclophosphamide and the neutrophil elimination/repopulation kinetics was monitored for 10 days. Basal white blood cell number and cellular composition was not different between WT controls and CCL3$^{-/-}$ mice. CCL3 deficient cells were slightly more sensitive to cyclophosphamide treatment (FIG. 20A,B) as white blood cell half life was significantly enhanced in CCL3$^{-/-}$ mice compared to WT (1.09±0.07 days in WT compared to 0.89±0.06 days in CCL3$^{-/-}$; p=0.04, FIG. 20C) and appeared equally distributed over the neutrophil and lymphocyte subset (FIG. 20C). Thus CCL3 deficient mice show a decreased neutrophil half life which concurs with the reduced numbers of circulating and plaque neutrophils in this strain. Repopulation of cells initiated 5 days post injection and was similar between CCL3$^{-/-}$ and WT controls (FIG. 20D)

Next we assessed the chemotactic response of WT and CCL3$^{-/-}$ neutrophils towards a gradient of the major chemokine in neutrophil recruitment, KC. Two hours after i.p. injection of KC, WBCs and peritoneal leukocytes were isolated and analyzed for neutrophil content. Circulating neutrophil numbers were similar between WT and CCL3$^{-/-}$ animals (6.1±1.0 in WT compared to 5.3±1.0 in CCL3$^{-/-}$, FIG. 21A). Surprisingly, given the reduced circulating neutrophil numbers, CCL3$^{-/-}$ animals had slightly enhanced neutrophil numbers in the peritoneum under normal conditions (0.6±0.5% in WT compared to 1.4±0.07, p=0.2, data not shown). KC injections robustly induced neutrophil migration towards the peritoneum of control animals. Peritoneal neutrophil counts after KC injections in CCL3$^{-/-}$ animals were only marginally lower compared to WT animals (12.3±0.4 in controls compared to 10.2±1.9 in CCL3$^{-/-}$ animals, data not shown). However the induction of neutrophil influx was decreased in CCL3$^{-/-}$ animals (20× induction in WT compared to 7.5× induction in CCL3$^{-/-}$, p=0.003; FIG. 21C), suggestive of impaired chemotaxis of CCL3$^{-/-}$ neutrophils under conditions of inflammation.

Interestingly plaque formation was attenuated as a result of leukocyte specific absence of CCL3, which may be due to a decreased accumulation of neutrophils in the plaque. Collectively our data indicate that deficiency of CCL3 will translate in a reduced neutrophil half life and to a impaired CXCR2 dependent accumulation of neutrophils in the plaque, which subsequently will translate into attenuated plaque progression.

Discussion

Chemokine mediated migration of leukocytes into the vessel wall is an essential step in atherosclerotic lesion formation and progression[5]. The CC chemokine CCL3 can interact with chemokine receptors CCR4, CCR1 and CCR5, of which the latter two have been implicated in atherogenesis. Combined with the upregulated aortic expression during atherogenesis[6], and its potent chemotactic effect on T cells, macrophages and neutrophilsTNF-α[7], a role of this chemokine in atherogenesis is conceivable. Here we show that leukocytes are the prime source of CCL3 under conditions of inflammation and that leukocyte CCL3 deficiency attenuates plaque development by altering neutrophil half life and reducing neutrophil accumulation.

In vitro experiments clearly established that activated macrophages are a rich source of CCL3, which is in concurrence with earlier data[8]. Moreover baseline levels of CCL3 in the circulation were seen to be only partly of leukocyte origin but almost exclusively produced by leukocytes during LPS elicited inflammatory responses[2,9]. Expression profiles of atherosclerotic lesion development revealed that CCL3 is mainly upregulated during early lesion progression, suggesting that CCL3 is involved in plaque inflammation[6]. Atherogenesis in CCL3$^{-/-}$ mice was significantly attenuated, but no effects on macrophage or T cell content were apparent. Interestingly, hematopoietic and systemic deficiency of one of the CCL3 receptors, CCR1, led to accelerated atherosclerosis[10,11]. CCR1 deficient plaques contained more macrophages and T cells and CCR1$^{-/-}$ T cells produced more IFNγ[10]. Conversely functional deficiency of CCR5, either in the hematopoietic lineage or systemically, was shown to reduce atherosclerotic lesion development and plaques contained less macrophages and T cells[11,12]. Antagonism of CCR5 by use of Met-RANTES similarly attenuated atherosclerosis development, macrophage and T cell content. Furthermore Met-Rantes treatment resulted in lower expression levels of CCR5, but not of its ligand CCL3[13]. CCL3 was shown to have a higher binding affinity for CCR5[14,15], suggestive that CCR5 mediated effects are primary during a chronic low rate inflammation, while acute substantial inflammation might correct these effects via CCR1 signalling. The phenotypic change seen in hematopoietic CCL3 deficiency seems to be more consistent with that of impaired CCR5 function, albeit that we did not see any noticeable effects on plaque macrophage content. This indicates that, although CCL3 might influence inflammatory cell migration, it is not crucial in monocyte or T cell migration towards the plaque.

Neutrophils were, until recently, not implicated in the pathogenesis of atherosclerosis. However more and more data are accumulating that support an active role of this subset of white blood cells in this disease. Naruka et al showed plaque neutrophil infiltrates to be associated with acute coronary events[16]. Experimental support came from van Leeuwen and coworkers showing the abundant presence of neutrophils in advanced mouse plaques[17], and from a collaborative expansion after blockage of CXCR4[18]. Plaque neutrophils are potent inflammatory cells acting in a narrow time span. Neutrophils are associated with increased intimal apoptosis and a pro-inflammatory phenotype[18]. Conceivably neutrophil accumulation in atherosclerotic lesions can induce plaque destabilization as a result of enhanced inflammation, necrotic core formation as a consequence of oxidative injury and matrix degradation by release of neutrophil elastases. CCL3 has been reported to be able to augment neutrophil chemotaxis induced by the pro-inflammatory cytokine TNFα in a CCR5 dependent manner[7]. In concurrence with these findings we show attenuated neutrophil migration to and diapedesis into the plaque in hematopoietic CCL3 deficiency. Moreover in vivo neutrophil migration towards KC (murine IL8 analogue) was reduced in CCL3$^{-/-}$ mice. This indicates that IL-8, similar to TNFα, can induce CCL3 mediated neutrophil migration.

Another intriguing option is that CCL3 affects neutrophil homeostasis. During inflammation, circulating neutrophil numbers were significantly lower in CCL3$^{-/-}$ mice, which fits well with the notion that apoptosis of neutrophils is regarded as a protective measure to dampen acute inflammatory responses and prevent unwanted tissue damage[19]. Terminally matured neutrophils therefore show a sharply reduced half life. Moreover, they have impaired migration and degranulation[20,21]. We observed a clear effect of CCL3−/− on neutrophil elimination kinetics, as the half life of CCL3 deficient neutrophils was decreased. However repopulation of neutrophils was not influenced by CCL3 deficiency, showing that neutrophil maturation and stromal release per se are not influenced. These data suggest that CCL3$^{-/-}$ neutrophils are more sensitive to cyclophosphamide, and perhaps other pro-apoptotic signals leading to a reduced half life.

Taken together our data clearly establish a causal role for neutrophils in the development of atherosclerosis. Furthermore we hypothesize that under conditions of inflammation leukocyte derived CCL3 can, possibly in concert with TNFα, alter neutrophil homeostasis and enhance neutrophil chemotaxis towards the atherosclerotic plaque to accelerate lesion formation.

TABLE 8

RT-PCR primer sequences and sources.

| Gene | forward primer (5'-3') | reverse primer (5'-3') |
|---|---|---|
| CCL3 | GCCACATCGAGGGACTCTTCA | GATGGGGGTTGAGGAACGTG |
| CD36 | GTTCTTCCAGCCAATGCCTTT | ATGTCTAGCACACCATAAGATGTACAGTT |
| CD68 | CCTCCACCCTCGCCTAGTC | TTGGGTATAGGATTCGGATTTGA |
| HPRT | TTGCTCGAGATGTCATGAAGGA | AGCAGGTCAGCAAAGAACTTATAG |
| CypA | CCATTTCAAGAAGCAGCGTTT | ATTTTGTCTTAACTGGTGGGTCTGT |

REFERENCES 1. von der Thusen J H, van Berkel T J, Biessen E A. Induction of rapid atherogenesis by perivascular carotid collar placement in apolipoprotein E-deficient and low-density lipoprotein receptor-deficient mice. *Circulation*. Feb. 27, 2001; 103(8):1164-1170.
2. Kasama T, Strieter R M, Standiford T J, et al. Expression and regulation of human neutrophil-derived macrophage inflammatory protein 1 alpha. *J Exp Med*. Jul. 1, 1993; 178(1):63-72.
3. Zuluaga A F, Salazar B E, Rodriguez C A, et al. Neutropenia induced in outbred mice by a simplified low-dose cyclophosphamide regimen: characterization and applicability to diverse experimental models of infectious diseases. *BMC Infect Dis*. 2006; 6:55.
4. Spellberg B J, Collins M, French S W, et al. A phagocytic cell line markedly improves survival of infected neutropenic mice. *J Leukoc Biol*. August 2005; 78(2):338-344.
5. Charo I F, Taubman M B. Chemokines in the pathogenesis of vascular disease. *Circ Res*. Oct. 29, 2004; 95(9):858-866.
6. Moos M P, John N, Grabner R, et al. The lamina adventitia is the major site of immune cell accumulation in standard chow-fed apolipoprotein E-deficient mice. *Arterioscler Thromb Vasc Biol.* November 2005; 25(11):2386-2391.
7. Montecucco F, Steffens S, Burger F, et al. Tumor necrosis factor-alpha (TNF-alpha) induces integrin CD11b/CD18 (Mac-1) up-regulation and migration to the CC chemokine CCL3 (MIP-1alpha) on human neutrophils through defined signalling pathways. *Cell Signal.* March 2008; 20(3):557-568.
8. Fahey T J, 3rd, Tracey K J, Tekamp-Olson P, et al. Macrophage inflammatory protein 1 modulates macrophage function. *J Immunol.* May 1, 1992; 148(9):2764-2769.
9. Harrison L M, van den Hoogen C, van Haaften W C, et al. Chemokine expression in the monocytic cell line THP-1 in response to purified shiga toxin 1 and/or lipopolysaccharides. *Infect Immun. January* 2005; 73(1):403-412.
10. Potteaux S, Combadiere C, Esposito B, et al. Chemokine receptor CCR1 disruption in bone marrow cells enhances atherosclerotic lesion development and inflammation in mice. *Mol Med.* January-December 2005; 11(1-12):16-20.
11. Potteaux S, Combadiere C, Esposito B, et al. Role of bone marrow-derived CC-chemokine receptor 5 in the development of atherosclerosis of low-density lipoprotein receptor knockout mice. *Arterioscler Thromb Vasc Biol.* August 2006; 26(8):1858-1863.
12. Braunersreuther V, Zernecke A, Arnaud C, et al. Ccr5 but not Ccr1 deficiency reduces development of diet-induced atherosclerosis in mice. *Arterioscler Thromb Vasc Biol.* February 2007; 27(2):373-379.
13. Veillard N R, Kwak B, Pelli G, et al. Antagonism of RANTES receptors reduces atherosclerotic plaque formation in mice. *Circ Res.* Feb. 6, 2004; 94(2):253-261.
14. Neote K, DiGregorio D, Mak J Y, et al. Molecular cloning, functional expression, and signaling characteristics of a C-C chemokine receptor. *Cell.* Feb. 12, 1993; 72(3):415-425.
15. Samson M, Labbe O, Mollereau C, et al. Molecular cloning and functional expression of a new human CC-chemokine receptor gene. *Biochemistry.* Mar. 19, 1996; 35(11):3362-3367.
16. Naruko T, Ueda M, Haze K, et al. Neutrophil infiltration of culprit lesions in acute coronary syndromes. *Circulation.* Dec. 3, 2002; 106(23):2894-2900.
17. van Leeuwen M, Gijbels M J, Duijvestijn A, et al. Accumulation of myeloperoxidase-positive neutrophils in atherosclerotic lesions in LDLR-/- mice. *Arterioscler Thromb Vasc Biol.* January 2008; 28(1):84-89.18
18. Zernecke A, Bot I, Djalali-Talab Y, et al. Protective role of CXC receptor 4/CXC ligand 12 unveils the importance of neutrophils in atherosclerosis. *Circ Res.* Feb. 1, 2008; 102 (2):209-217.
19. Luo H R, Loison F. Constitutive neutrophil apoptosis: mechanisms and regulation. *Am J Hematol.* April 2008; 83(4):288-295.
20. Savill J. Apoptosis in resolution of inflammation. *J Leukoc Biol.* April 1997; 61(4):375-380.
21. Whyte M K, Meagher L C, MacDermot J, et al. Impairment of function in aging neutrophils is associated with apoptosis. *J Immunol.* Jun. 1, 1993; 150(11):5124-5134.

The invention claimed is:

1. A method for identifying a subject at increased risk of a future acute cardiovascular syndrome or event, the method comprising:
   a) obtaining a sample from a subject;
   b) determining an amount of at least one compound selected from the group consisting of CCL3 (chemokine (C-C motif) ligand 3), CCL18 (chemokine (C-C motif) ligand 18), and CCL5 (chemokine (C-C motif) ligand 5) by contacting the sample with:
      i) an antibody specific for CCL3, and quantifying the amount of CCL3 bound to the antibody,
      ii) an antibody specific for CCL18, and quantifying the amount of CCU18 bound to the antibody, or
      iii) an antibody specific for CCL5, and quantifying the amount of CCL5 bound to the antibody;
   c) identifying a subject as having an increased risk of a future acute cardiovascular syndrome or event if the sample from the subject was determined to have greater than 41 pg/ml CCL3, greater than 40.3 ng/ml CCL5, or greater than 39.3 ng/ml CCL18; and d) performing follow-up on the subject identified with an increased risk using standard medical therapy.

2. The method according to claim 1, wherein the cardiovascular syndrome or event may comprise coronary artery disease, atherosclerosis, acute myocardial infarction, arteriosclerosis, unstable angina pectoris, embolism, deep vein thrombosis, stroke, congestive heart failure or arrhythmia.

3. The method according to claim 1, wherein the indication of an increased risk of a future acute cardiovascular syndrome or event may be used for monitoring the status and/or progression of said syndrome or event.

4. The method according to claim 1, wherein the indication of an increased risk of a future acute cardiovascular syndrome or event may be used for monitoring therapeutic regimes and/or clinical trials in order to detect whether or not a particular treatment may be effective in reducing an increased risk of an acute cardiovascular syndrome or event.

5. The method according to claim 1, wherein the sample is a cell taken from the subject or a sample of a body fluid of the subject, which may be derived from blood or from a blood fraction.

6. The method according to claim 1, wherein the amount of compound bound to an antibody is detected by a method selected from the group consisting of an immunoassay, an enzyme linked immunoassays (ELISA), a fluorescence based assays, a dissociation enhanced lanthanide fluoroimmunoassay (DELFIA), a radiometric assays, a multiplex immunoassays, and a cytrometric bead assays (CBA).

7. The method according to claim 1, further comprising assessing clinical symptoms, determining the level of at least one other compound in the subject, or a combination thereof, wherein the at least one other compound is a biomarker indicative of cardiovascular disease or a predisposition thereto.

8. The method according to claim 7, wherein the at least one other compound is selected from the group consisting of CXSCL 10 (IP-10), C-Reactive Protein, troponin I, creatine kinase, creatine kinase MB, CD40L, high density lipoprotein (HDL), myoglobin and interleukin-6.

9. A method for identifying a subject at increased risk of a future acute cardiovascular syndrome or event, which method comprises:
   a) determining a level of at least one compound selected from the group consisting of CCL3, CCL18, and CCL5, in a sample from a subject to be tested using a method selected from the group consisting of an immunoassay, an enzyme linked immunoassays (ELISA), a fluorescence based assays, a dissociation enhanced lanthanide fluoroimmunoassay (DELFIA), a radiometric assays, a multiplex immunoassays and a cytrometric bead assays (CBA);
   b) identifying a subject as having an increased risk of a future acute cardiovascular syndrome or event if the sample from the subject was determined to have greater than 41 pg/ml CCL3, greater than 40.3 ng/ml CCL5, or greater than 39.3 ng/ml CCL18; and
   c) performing follow-up on the subject identified with an increased risk using standard medical therapy.

10. A method for identifying a subject at increased risk of a future acute cardiovascular syndrome or event, the method comprising:
   a) obtaining a sample from a subject;
   b) determining an amount of each compound selected from the group consisting of CCL3 (chemokine (C-C motif) ligand 3), CCL18 (chemokine (C-C motif) ligand 18), and CCL5 (chemokine (C-C motif) ligand 5) by contacting the sample with:
      i) an antibody specific for CCL3, and quantifying the amount of CCL3 bound to the antibody,
      ii) an antibody specific for CCL18, and quantifying the amount of CCL18 bound to the antibody, and
      iii) an antibody specific for CCL5, and quantifying the amount of CCL5 bound to the antibody;
   c) identifying a subject as having an increased risk of a future acute cardiovascular syndrome or event if the sample from the subject was determined to have greater than 41 pg/ml CCL3, greater than 40.3 ng/ml CCL5, and greater than 39.3 ng/ml CCL18; and
   d) performing follow-up on the subject identified with an increased risk using standard medical therapy.

11. The method of claim 10, wherein the subject is identified as having an increased risk of a future acute cardiovascular syndrome or event if the sample from the subject was determined to have greater than 53 pg/ml CCL3.

12. The method of claim 10, wherein the subject is identified as having an increased risk of a future acute cardiovascular syndrome or event if the sample from the subject was determined to have greater than 83 pg/ml CCL3.

13. The method of claim 10, wherein the subject is identified as having an increased risk of a future acute cardiovascular syndrome or event if the sample from the subject was determined to have greater than 66 ng/ml CCL18.

14. The method of claim 10, wherein the subject is identified as having an increased risk of a future acute cardiovascular syndrome or event if the sample from the subject was determined to have greater than 130 ng/ml CCL18.

15. The method of claim 10, wherein the subject is identified as having an increased risk of a future acute cardiovascular syndrome or event if the sample from the subject was determined to have greater than 53 pg/ml CCL3, greater than 40.3 CCL5, and greater than 66 ng/ml CCL18.

16. The method of claim 10, wherein the sample is selected from the group consisting of blood and serum.

* * * * *